United States Patent
Reddy et al.

(10) Patent No.: US 8,143,453 B2
(45) Date of Patent: Mar. 27, 2012

(54) UNSATURATED SULFIDES, SULFONES, SULFOXIDES AND SULFONAMIDES SYNTHESIS

(75) Inventors: M. V. Ramana Reddy, Upper Darby, PA (US); E. Premkumar Reddy, Villanova, PA (US); Stanley C. Bell, Narberth, PA (US)

(73) Assignees: Temple University—Of The Commonwealth System of Higher Education, Philadelphia, PA (US); Onconova Therapeutics, Inc., Newtown, PA (US)

( * ) Notice: Subject to any disclaimer, the term of this patent is extended or adjusted under 35 U.S.C. 154(b) by 1155 days.

(21) Appl. No.: 11/884,601

(22) PCT Filed: Feb. 24, 2006

(86) PCT No.: PCT/US2006/006698
§ 371 (c)(1),
(2), (4) Date: Sep. 24, 2007

(87) PCT Pub. No.: WO2006/091870
PCT Pub. Date: Aug. 31, 2006

(65) Prior Publication Data
US 2009/0124828 A1      May 14, 2009

Related U.S. Application Data

(60) Provisional application No. 60/656,204, filed on Feb. 25, 2005.

(51) Int. Cl.
*C07C 315/00* (2006.01)
(52) U.S. Cl. ............. 568/30; 568/27; 568/28; 568/31; 564/86
(58) Field of Classification Search ............... None
See application file for complete search history.

(56) References Cited

U.S. PATENT DOCUMENTS

| | | | |
|---|---|---|---|
| 4,246,263 A | 1/1981 | Lombardino et al. | 424/251 |
| 6,201,154 B1 | 3/2001 | Reddy et al. | 568/28 |
| 6,359,013 B1 | 3/2002 | Reddy et al. | 514/710 |
| 6,414,034 B1 | 7/2002 | Reddy et al. | 514/710 |
| 6,486,210 B2 | 11/2002 | Reddy et al. | 514/708 |
| 6,541,475 B2 | 4/2003 | Reddy et al. | 514/252.12 |
| 6,548,553 B2 | 4/2003 | Reddy et al. | 514/710 |
| 6,576,675 B1 | 6/2003 | Reddy et al. | 514/710 |
| 6,599,932 B1 | 7/2003 | Reddy et al. | 514/438 |
| 6,656,973 B2 | 12/2003 | Cosenza et al. | 514/710 |
| 6,667,346 B2 | 12/2003 | Reddy et al. | 514/710 |
| 6,762,207 B1 | 7/2004 | Reddy et al. | 514/709 |

FOREIGN PATENT DOCUMENTS
CN     1332139     1/2002

OTHER PUBLICATIONS

Vedula et al, European Journal of Medicinal Chemistry, 2003, 38, 811-824.*
Clive et al, Journal of Organic Chemistry, 2003, 68(24), 9247-9254.*
Benati, et al., "Free-Radical Addition of Alkanethiols to Alkynes. Rearrangements of the Intermediate β-Thiovinyl Radicals", *J. Org. Chem.* 1994, 59, 2818-2823.
Clive, et al., "Derivatized Amino Acids Relevant to Native Peptide Synthesis by Chemical Ligation and Acyl Transfer", *J. Org. Chem.*, vol. 68, 2003, pp. 9247-9254.
Kageyama, et al., "Sodium Bromite: A New Selective Reagent for the Oxidation of Sulfides and Alcohols", *Synthesis*, 1983, pp. 815-816.
Node, et al., "A Raney Nickel—Sodium Hypophosphite Combination System for Reductive Desulfurization without Racemization of Optically Active Secondary Alcohol", *Tetrahedron*, vol. 53, No. 38, pp. 12883-12894, 1997.
Pasto, et al., "Transfer Reactions Involving Boron. III. Hydroboration Studies with Enethiol Ethers", *J. Am. Soc. Soc.*, vol. 85, 1963, pp. 2118-2124.
Vedula et al., "New styryl sulfones as anticancer agents", *European Journal of Medicinal Chemistry*, 2003, 38(9): 811-824.
Reddy et al., "Synthesis of α,β-Unsaturated Sulfones", *Acta Chimica Hungarica*, 1984, 115(3): 269-271.
Reddy et al., "A Novel Synthesis of (E)-Substituted Styryl (Z)-Styryl Sulfones", *Synthesis*, 1984, (4): 311-323.
Reddy et al., "A Facile Method for the Synthesis of 2-(Arylsulfonyl)-1-Phenyl-3-Aryl-2-Propen-1-Ones", *Sulfur Letters*, 1987, 7(2): 43-48.
Reddy et al., "Synthesis and Cyclopropanation of (E)-And (Z)-Styryl Benzyl Sulfones", *Sulfur Letters*, 1991, 13(2): 83-90. (Abstract).
Database Beilstein, Beilstein Institute for Organic Chemistry, Frankfurt-Main, DE; 2000 "(E)-Benzyl styryl sulfoxide", Database accession no. 8833005.

* cited by examiner

*Primary Examiner* — Sudhakar Katakam
(74) *Attorney, Agent, or Firm* — Drinker Biddle & Reath LLP

(57) ABSTRACT

α,β-Unsaturated sulfides, sulfones, sulfoxides and sulfonamides according to Formula I:

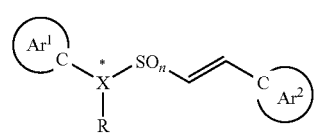

wherein $Ar^1$, $Ar^2$, X, n, * and R are as defined herein, are prepared by dehydration of β-hydroxy sulfides, sulfones, sulfoxides or sulfonamides.

9 Claims, No Drawings

UNSATURATED SULFIDES, SULFONES, SULFOXIDES AND SULFONAMIDES SYNTHESIS

FIELD OF THE INVENTION

The invention relates to a process for the preparation of α,β-unsaturated sulfides, sulfones, sulfoxides and sulfonamides via intermediate β-ketosulfides, β-ketosulfones, β-ketosulfoxides and β-ketosulfonamides, respectively.

BACKGROUND OF THE INVENTION

Certain α,β-unsaturated sulfones, sulfoxides and sulfonamides particularly styrylbenzyl sulfones have been shown to possess antiproliferative, radioprotective and chemoprotective activity. See U.S. Pat. Nos. 6,599,932, 6,576,675, 6,548,553, 6,541,475, 6,486,210, 6,414,034, 6,359,013, 6,201,154, 6,656,973 and 6,762,207, the entire disclosures of which are incorporated herein by reference.

(E)-α,β-unsaturated sulfones have been prepared, for example, by Knoevenagel condensation of aromatic aldehydes with sulfones such as 2-(arylmethylsulfonyl)acetic acids. The procedure is described for the synthesis of the styryl sulfones by Reddy et al., *Acta. Chim. Hung.* 115:269-71 (1984); Reddy et al., *Sulfur Letters* 13:83-90 (1991); Reddy et al., *Synthesis* No. 4, 322-323 (1984); and Reddy et al., *Sulfur Letters* 7:43-48 (1987), the entire disclosures of which are incorporated herein by reference.

Alternative synthetic methods for preparing (E)-α,β-unsaturated sulfides, sulfones, sulfoxides and sulfonamides are desired.

SUMMARY OF THE INVENTION

I. Methods of Preparation

As one aspect of the invention, chemical processes are provided for the preparation of certain compounds of Formula I, or salts thereof, having useful antiproliferative activity and for the preparation of intermediates useful in the preparation of such compounds.

A process is provided for the preparation of a compound according to Formula I, or a salt thereof:

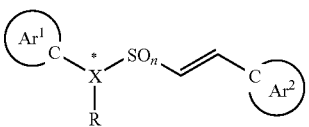

wherein:
Ar¹ and Ar² are independently selected from substituted and unsubstituted aryl and substituted and unsubstituted heteroaryl;
X is N or CH;
n is 0, 1 or 2, preferably 1 or 2, more preferably 2;
R is —H or —($C_1$-$C_8$)hydrocarbyl; and
* indicates that, when X is CH, and R is other than —H, the configuration of the substituents on the carbon atom of X is (R)—, (S)— or any mixture of (R)— and (S)—;
provided that when X is N, then n is 2;
comprising the steps of:
(a) reacting a compound according to Formula II, or a salt thereof:

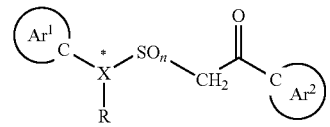

wherein, Ar¹, Ar², R, n, X and * are as defined above for Formula I, under conditions sufficient to reduce the ketone moiety of the Formula II compound to a secondary alcohol, to form a compound according to Formula III, or a salt thereof:

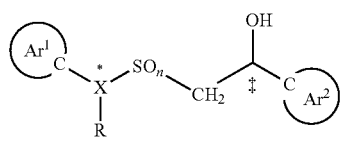

wherein Ar¹, Ar², X, n, * and R are as defined for compounds according to Formula I, and ‡ indicates that the configuration of the substituents on the designated carbon atom is (R)—, (S)— or any mixture of (R)— and (S)—;

(b) reacting said compound according to Formula III prepared in step (a), or a salt thereof, under conditions sufficient to dehydrate the secondary alcohol moiety of the Formula III compound to form a compound according to Formula I, or a salt thereof; and (c) isolating said compound according to Formula I formed in step (b), or a salt thereof, from the reaction mixture of step (b).

The compound according to Formula III, or a salt thereof, may optionally be isolated prior to performing the dehydration reaction of Step (b), or the dehydration step may be carried out without isolation of the intermediate compound of Formula M.

According to preferred embodiments of the invention, substituents on substituted aryl or heteroaryl Ar¹ may be independently selected from the group consisting of halogen, —($C_1$-$C_8$)hydrocarbyl, —C(=O)$R^2$, —N$R^2_2$, —NHC(=O)$R^3$, —NHSO$_2R^3$, —NH($C_2$-$C_6$)alkylene-C(=O)$R^6$, —NHC$R^2R^4$C(=O)$R^6$, —C(=O)O$R^2$, —C(=O)N$R^2_2$, —NO$_2$, —C≡N, —O$R^2$, —OC(=O)$R^3$, —OSO$_2R^3$, —O($C_2$-$C_6$)alkylene-C(=O)$R^6$, —OC$R^2R^4$C(=O)$R^6$, —P(=O)(O$R^2$)$_2$, —OP(=O)(O$R^2$)$_2$, —O($C_2$-$C_6$)alkylene-N(($C_1$-$C_3$)alkyl)$_2$, —NHC(=NH)NH$R^2$, —($C_1$-$C_6$)haloalkyl, —O($C_1$-$C_6$)haloalkyl and —N=CH—$R^7$; and substituents on substituted aryl or substituted heteroaryl Ar² may be independently selected from the group consisting of —($C_1$-$C_8$)hydrocarbyl, —C(=O)$R^2$, halogen, —NO$_2$, —C≡N, —O$R^2$, —C(=O)O$R^2$, —N$R^2_2$, —($C_1$-$C_6$)haloalkyl and —O($C_1$-$C_6$)haloalkyl;

wherein:
each $R^2$ is independently selected from the group consisting of —H and —($C_1$-$C_8$)hydrocarbyl;
each $R^3$ is independently selected from the group consisting of —($C_1$-$C_8$)hydrocarbyl, —O($C_1$-$C_8$)hydrocarbyl, substituted and unsubstituted aryl, substituted and unsubstituted heterocyclyl($C_1$-$C_3$)alkyl, substituted and unsubstituted heteroaryl($C_1$-$C_3$)alkyl, —($C_2$-$C_{10}$)heteroalkyl, —($C_1$-$C_6$)haloalkyl, —C$R^2R^4$NH$R^5$, —N$R^2_2$, —($C_1$-$C_3$)alkyleneNH$_2$, —($C_1$-$C_3$)alkylene-N(($C_1$-$C_3$)alkyl)$_2$, —($C_1$-$C_3$)perfluoroalkylene-N(($C_1$-$C_3$)alkyl)$_2$, —($C_1$-$C_3$)alkylene-N⁺(($C_1$-$C_3$)

allyl)$_3$, —(C$_1$-C$_3$)alkylene-N$^+$(CH$_2$CH$_2$OH)$_3$, —(C$_1$-C$_3$)alkylene-OR$^2$, —(C$_1$-C$_4$)alkylene-CO$_2$R$^2$, —(C$_1$-C$_4$)alkylene-C(=O)halogen, halo(C$_1$-C$_3$)alkyl-, —(C$_1$-C$_3$)alkylene-C(=O)(C$_1$-C$_3$)allyl, and —(C$_1$-C$_4$)perfluoroalkylene-CO$_2$R$^2$;

each R$^4$ is independently selected from the group consisting of —H, —(C$_1$-C$_6$)alkyl, —(CH$_2$)$_3$—NH—C(NH$_2$)(=NH), —CH$_2$C(=O)NH$_2$, —CH$_2$CO$_2$R$^2$, —CH$_2$SH, —(CH$_2$)$_2$C(=O)—NH$_2$, —(CH$_2$)$_2$CO$_2$R$^2$, —CH$_2$-(2-imidazolyl), —(CH$_2$)$_4$—NH$_2$, —(CH$_2$)$_2$—S—CH$_3$, phenyl, —CH$_2$-phenyl, —CH$_2$—OH, —CH(OH)—CH$_3$, —CH$_2$-(3-indolyl), and —CH$_2$(4-hydroxyphenyl);

each R$^5$ is independently selected from the group consisting of —H, —C(=O)(C$_1$-C$_7$)hydrocarbyl and a carboxy terminally-linked peptidyl residue containing from 1 to 3 amino acids in which the terminal amino group of the peptidyl residue is present as a functional group selected from the group consisting of —NH$_2$, —NHC(=O)(C$_1$-C$_6$)alkyl, —NH(C$_1$-C$_6$)alkyl, —N((C$_1$-C$_8$)alkyl)$_2$ and —NHC(=O)O(C$_1$-C$_7$)hydrocarbyl;

each R$^6$ is independently selected from the group consisting of —OR$^2$, —NR$^2_2$, and an amino terminally-linked peptidyl residue containing from 1 to 3 amino acids in which the terminal carboxyl group of the peptidyl residue is present as a functional group selected from the group consisting of —CO$_2$R$^2$ and —C(=O)NR$^2_2$; and each R$^7$ is independently selected from the group consisting of substituted and unsubstituted aryl and substituted and unsubstituted heteroaryl;

provided that the highest number of substituents on Ar$^1$ and Ar$^2$ is equal to the number of substitutable hydrogen atoms in the ring to which the substituents are attached.

Substituents on substituted aryl or heteroaryl groups that comprise R$^3$ or R$^7$ are preferably independently selected from the group consisting of —(C$_1$-C$_6$)alkyl, —(C$_1$-C$_6$)alkoxy, halogen, —C(=O)(C$_1$-C$_6$)alkyl, —NH$_2$, —NH(C$_1$-C$_6$)alkyl, —N((C$_1$-C$_6$)alkyl)$_2$, —NHC(=O)(C$_1$-C$_6$)alkyl, —NO$_2$, —C≡N, (C$_1$-C$_6$)haloalkyl, —(C$_1$-C$_6$)alkylene-NH$_2$, —CO$_2$H, —CONH$_2$, —C(=NH)NH$_2$, and heterocyclyl(C$_1$-C$_6$)alkyl; wherein heterocyclyl rings comprising heterocyclyl(C$_1$-C$_6$)alkyl are optionally substituted by —(C$_1$-C$_6$)alkyl or C(=O)(C$_1$-C$_6$)alkyl.

Substituents on substituted heterocyclyl groups that comprise R$^3$ are preferably independently selected from the group consisting of —(C$_1$-C$_6$)alkyl, —(C$_1$-C$_6$)alkoxy, halogen, —C(=O)(C$_1$-C$_6$)alkyl, —CO$_2$H, and CONH$_2$.

According to some preferred embodiments of the invention, Ar$^1$ is phenyl. According to other preferred embodiments of the invention, Ar$^2$ is phenyl. According to still other preferred embodiments of the invention, both Ar$^1$ and Ar$^2$ are phenyl.

Preferably, when Ar$^1$ and Ar$^2$ are both phenyl, both Ar$^1$ and Ar$^2$ are at least mono-substituted.

According to some embodiments, the aryl and heteroaryl groups comprising Ar$^1$ and Ar$^2$ are mono-, di- or tri-substituted. According to other embodiments, the aryl and heteroaryl groups comprising Ar$^1$ and Ar$^2$ are substituted at all substitutable positions.

R is preferably —H or —(C$_1$-C$_8$)alkyl, more preferably —H or —(C$_1$-C$_6$)alkyl, most preferably —H.

According to particularly preferred embodiments of the invention, the compound according to Formula I which is prepared according to the process of the invention is selected from the group consisting of: (E)-5-(2,4,6-trimethoxystyrylsulfonamido)-2-methoxyphenol; 5-({[(1E)-2-(2,4,6-trimethoxy-phenyl)vinyl]sulfonyl}amino)-2-methoxyphenylamine; 2-[5-({[(1E)-2-(2,4,6-trimethoxyphenyl)vinyl]sulfonyl}amino)-2-methoxy-phenylamino]acetic acid; (E)-N-phenyl-4-fluorostyryl sulfonamide; (E)-N-phenyl-4-iodostyrylsulfonamide; (E)-N-phenyl-4-chlorostyrylsulfonamide; (E)-N-4-methoxyphenyl-4-chlorostyrylsulfonamide; (E)-N-4-methoxyphenyl-styrylsulfonamide; (E)-N-4-methoxyphenyl-4-methoxystyrylsulfonamide; (E)-N-4-chlorophenyl-4-chlorostyrylsulfonamide; (E)-N-4-chlorophenyl-4-fluorostyrylsulfonamide; (E)-N-4-chlorophenyl-4-bromostyrylsulfonamide; (E)-5-((2,4,6-trimethoxystyrylsulfonyl)-methyl)-2-methoxyphenol; (E)-2-(5-((2,4,6-trimethoxystyrylsulfonyl)methyl)-2-methoxyphenylamino)propanoic acid; (E)-5-((2,4,6-trimethoxystyryl sulfonyl)methyl)-2-methoxybenzenamine; (E)-2-(5-((2,4,6-trimethoxystyrylsulfonyl)methyl)-2-methoxyphenylamino)acetic acid; 1-((E)-2-(benzylsulfonyl)vinyl)-4-fluorobenzene; 1-((E)-2-(benzylsulfonyl)vinyl)-4-iodobenzene; 1-((E)-2-(benzylsulfonyevinyl)-4-chlorobenzene; (E)-1-((4-chlorostyrylsulfonyl)methyl)-4-methoxybenzene; (E)-1-methoxy-4-((styrylsulfonyl)methyl)benzene; (E)-1-((4-methoxystyrylsulfonyl)methyl)-4-methoxybenzene; (E)-1-((4-chlorostyrylsulfonyl)methyl)-4-chlorobenzene; (E)-1-((4-fluorostyrylsulfonyl)methyl)-4-chlorobenzene; (E)-1-((4-bromostyrylsulfonyl)methyl)-4-chlorobenzene; (E)-2-(5-((2,4,6-trimethoxystyrylsulfonyl)methyl)-2-methoxyphenylamino)-2-phenylacetic acid; (E)-5-((2,4,6-trimethoxystyrylsulfinyl)methyl)-2-methoxyphenol; (E)-2-(5-((2,4,6-trimethoxystyrylsulfinyemethyl)-2-methoxyphenylamino)propanoic acid; (E)-5-(2,4,6-trimethoxystyrylsulfinyl)methyl)-2-methoxybenzenamine; (E)-2-(5-((2,4,6-trimethoxystyrylsulfinyl)methyl)-2-methoxyphenylamino)acetic acid; 1-((E)-2-(benzylsulfinyl)vinyl)-4-fluorobenzene; 1-((E)-2-(benzylsulfinyl)vinyl)-4-iodobenzene; 1-((E)-2-(benzylsulfinyl)vinyl)-4-chlorobenzene; (E)-1-((4-chlorostyrylsulfinyl)methyl)-4-methoxybenzene; (E)-1-methoxy-4-((styrylsulfinyl)methyl)benzene; (E)-1-((4-methoxystyrylsulfinyl)methyl)-4-methoxybenzene; (E)-1-((4-chlorostyrylsulfinyl)methyl)-4-chlorobenzene; (E)-1-((4-fluorostyrylsulfinyl)methyl)-4-chlorobenzene; (E)-1-((4-bromostyrylsulfinyl)methyl)-4-chlorobenzene; (E)-2-(5-((2,4,6-trimethoxystyrylsulfinyl)-methyl)-2-methoxyphenylamino)-2-phenylacetic acid; (E)-5-((2,4,6-trimethoxy-styrylthio)methyl)-2-methoxyphenol; (E)-2-(5-((2,4,6-trimethoxystyrylthio)methyl)-2-methoxyphenylamino)propanoic acid; (E)-5-((2,4,6-trimethoxystyrylthio)methyl)-2-methoxybenzenamine; (E)-2-(5-((2,4,6-trimethoxystyrylthio)methyl)-2-methoxyphenylamino)acetic acid; (E)-(4-fluorostyryl)(benzyl)sulfane; (E)-(4-iodostyryl)(benzyl)sulfane; (E)-(4-chlorostyryl)(benzyl)sulfane; (E)-(4-chlorostyryl)(4-methoxybenzyl)sulfane; (E)-(4-methoxybenzyl)(styryl)sulfane; (E)-(4-methoxybenzyl)(4-methoxystyryl)sulfane; (E)-(4-chlorobenzyl)(4-chlorostyryl)sulfane; (E)-(4-chlorobenzyl)(4-fluorostyryl)sulfane; (E)-(4-bromostyryl)(4-chlorobenzyl)sulfane; (E)-2-(5-((2,4,6-trimethoxystyrylthio)methyl)-2-methoxyphenylamino)-2-phenylacetic acid; and salts thereof.

According to other embodiments of the invention, compounds of Formula I wherein X is CH and n is 1 (α,β-unsaturated sulfoxides) and compounds of Formula I wherein X is CH and n is 2 (α,β-unsaturated sulfones), or salts thereof, may be prepared by oxidation processes wherein compounds according to Formula I, wherein n is 0, or salts thereof, are used as chemical intermediates.

According to one such embodiment, a compound according to Formula I, or a salt thereof, wherein:

Ar¹ and Ar² are independently selected from substituted and unsubstituted aryl and substituted and unsubstituted heteroaryl;

X is CH;

n is 1;

R is —H or —($C_1$-$C_8$)hydrocarbyl; and

\* indicates that, when R is other than —H, the configuration of the substituents on the carbon atom of X is (R)—, (S)— or any mixture of (R)— and (S)—;

provided that, when Ar² is unsubstituted phenyl, then Ar¹ is other than 4-($C_1$-$C_6$)alkoxyphenyl, is prepared by the steps of:

(a) reacting a compound according to Formula I, wherein Ar¹, Ar², X, \* and R are as defined above, and n is 0, or a salt thereof, with at least one oxidizing agent capable of oxidizing a sulfide to a sulfoxide; and (b) isolating a compound according to Formula I, wherein n is 1, or a salt thereof, from the reaction products.

According to another such embodiment, a compound according to Formula I, or a salt thereof, wherein:

Ar¹ and Ar² are independently selected from substituted and unsubstituted aryl and substituted and unsubstituted heteroaryl;

X is CH;

n is 2;

R is —H or —($C_1$-$C_8$)hydrocarbyl; and

\*indicates that, when R is other than —H, the configuration of the substituents on the carbon atom of X is (R)—, (S)— or any mixture of (R)— and (S)—;

provided that, when Ar² is unsubstituted phenyl, then Ar¹ is other than 4-($C_1$-$C_6$)alkoxyphenyl, is prepared by the steps of:

(a) reacting a compound according to Formula I, wherein Ar¹, Ar², X, \* and R are as defined above, and n is 0, or a salt thereof, with at least one oxidizing agent capable of oxidizing a sulfide to a sulfone; and (b) isolating a compound according to Formula I, wherein n is 2, or a salt thereof, from the reaction products.

According to another embodiment of the invention, compounds according to Formula II, or salts thereof, may be prepared, for example, by reacting a compound according to Formula IIc, or a salt thereof:

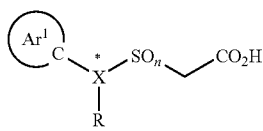

IIc wherein Ar¹, X, R, \* and n are as defined above for compounds according to Formula I, with a compound according to Formula IId, or a salt thereof:

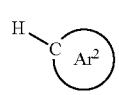

IId wherein Ar² is as defined above for compounds according to Formula I. The reaction of the Formula IIc and Formula IId compounds is carried out under conditions suitable for electrophilic acylation of the aromatic ring of Ar². A compound according to Formula II, or a salt thereof, is isolated from the reaction products.

A compound according to Formula IIe, wherein X is N and n is 2, or a salt thereof, may be prepared, for example, by a process comprising the steps of:

(a) reacting a compound according to Formula IIe, or a salt thereof:

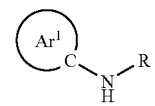

IIe wherein Ar¹ and R are as defined herein for compounds according to Formula I;

with a compound according to Formula IIf:

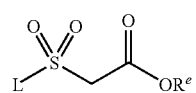

IIf wherein $R^e$ is —($C_1$-$C_6$)alkyl and L is a leaving group, preferably a halogen, more preferably —Cl or —Br; to form a compound according to Formula IIg, or a salt thereof:

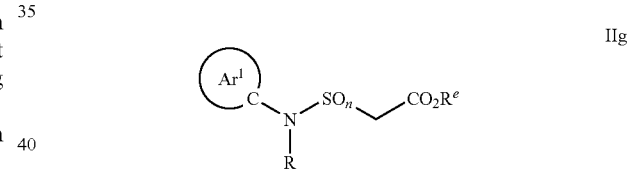

IIg wherein Ar¹ and R are as defined herein for compounds according to Formula I, n is 2, and $R^e$ is —($C_1$-$C_6$)alkyl; and (b) hydrolyzing the Formula IIg compound, formed in step (a), or a salt thereof, to form a compound according to Formula IIe, wherein X is N and n is 2, or a salt thereof.

Reagents suitable for hydrolysis of a Formula IIg compound include, for example one or more bases, preferably alkali metal hydroxides, carbonates or bicarbonates or alkaline earth metal hydroxides, carbonates or bicarbonates, more preferably, alkali metal hydroxides such as, for example, LiOH and NaOH.

Hydrolysis of a Formula IIg compound is preferably carried out in the presence of an aqueous solvent, more preferably a mixture of water with one or more water-miscible solvents selected from the group consisting of methanol, ethanol, acetonitrile, and tetrahydrofuran.

A compound according to Formula IIc, wherein X is CH and n is 0, or a salt thereof, may be prepared, for example, by a process comprising the steps of:

(a) reacting a compound according to Formula IIb, or a salt thereof:

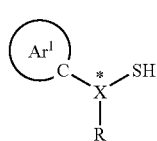

wherein X is CH, and Ar$^1$, * and R are as defined herein for Formula I compounds;

with a compound according to Formula IIh:

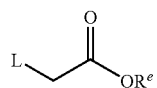

wherein R$^e$ is —(C$_1$-C$_6$)alkyl and L is a leaving group, preferably a halogen, more preferably —Cl or —Br;

to form a compound according to Formula IIi, or a salt thereof:

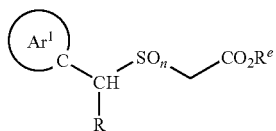

wherein Ar$^1$, R, n and R$^e$ are as defined above; and (b) hydrolyzing the compound according to Formula IIi, formed in step (a), or a salt thereof, to form a compound according to Formula IIc, wherein X is CH and n is 0, or a salt thereof.

Reagents and solvents suitable for hydrolysis of a Formula IIi compound are as described above for hydrolysis of a Formula IIg compound.

Compounds according to Formula IIk, wherein X is CH and n is 1, or salts thereof, may be prepared, for example, by a process comprising reacting a compound according to Formula IIe, wherein X is CH and n is 0, or a salt thereof, with an oxidizing agent capable of oxidizing a sulfide to a sulfoxide to form a compound according to Formula IIc; wherein X is CH and n is 1, or a salt thereof.

Compounds according to Formula IIc, wherein X is CH and n is 2, or salts thereof, may be prepared, for example, by a process comprising reacting a compound according to Formula IIc, wherein X is CH and n is 0, or a salt thereof, with an oxidizing agent capable of oxidizing a sulfide to a sulfone to form a compound according to Formula IIc, wherein X is CH and n is 2, or a salt thereof.

According to another embodiment of the invention, compounds according to Formula II, wherein X is CH and n is 0, and salts thereof, may be prepared, for example, by a process comprising the steps of:

(a) reacting a compound according to Formula IIa, or a salt thereof:

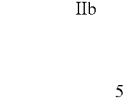

wherein Ar$^2$ is as defined as for compounds of Formula I, and L is a leaving group, with a compound according to Formula IIb, or a salt thereof:

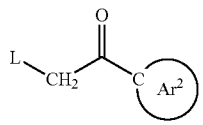

wherein X is CH, and Ar$^1$, * and R are as defined above for compounds according to Formula I; to form a compound according to Formula II, wherein X is CH and n is 0, or a salt thereof.

The compound according to Formula II, or a salt thereof, may optionally be isolated prior to proceeding with the use of the compound of Formula II in preparation of a compound according to Formula I. Alternatively, the process of preparing a compound according to Formula I, or a salt thereof, may be carried out without isolation of the intermediate compound of Formula II.

According to some embodiments of the invention, X is CH. According to some embodiments of the invention wherein X is CH, n is 0. According to other embodiments of the invention wherein X is CH, n is 1. According to still other embodiments of the invention wherein X is CH, n is 2.

According to one embodiment of the invention, compounds according to Formula II, wherein X is CH and n is 1, or salts thereof, may be prepared, for example, by a process comprising the steps of:

(a) reacting a compound according to Formula IIa, or a salt thereof:

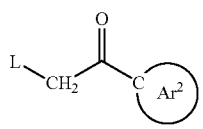

wherein Ar$^2$ is as defined as for compounds of Formula I, and L is a leaving group, with a compound according to Formula IIb, or a salt thereof:

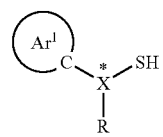

wherein X is CH, and Ar$^1$, * and R are as defined above for compounds according to Formula I, to form a compound according to Formula II, wherein X is CH and n is 0, or a salt thereof; and (b) reacting the compound according to Formula II formed in step (a), or a salt thereof, with an oxidizing agent capable of oxidizing a sulfide to a sulfoxide to form a compound according to Formula II, wherein X is CH and n is 1, or a salt thereof.

The compound according to Formula II formed in step (a), or a salt thereof, may optionally be isolated prior to reacting with an oxidizing agent in step (b), or the oxidation of step (b) may be done without isolation of the intermediate compound of Formula II.

According to another embodiment of the invention, compounds according to

Formula II, wherein X is CH and n is 2, or salts thereof, may be prepared, for example, by a process comprising the steps of:

(a) reacting a compound according to Formula IIa, or a salt thereof:

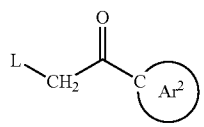

IIa wherein $Ar^2$ is as defined as for compounds of Formula I, and L is a leaving group;

with a compound according to Formula III), or a salt thereof:

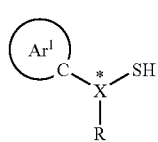

IIb wherein X is CH, and $Ar^1$, * and R are as defined above for compounds according to Formula I, to form a compound according to Formula II, wherein X is CH and n is 0, or a salt thereof; and (b) reacting the compound according to Formula II formed in step (a), or a salt thereof, with an oxidizing agent capable of oxidizing a sulfide to a sulfone to form a compound according to Formula II, wherein X is CH and n is 2, or a salt thereof.

II. Intermediates

According to another aspect of the invention, compounds are provided which are useful as intermediates in the processes described above for the preparation of compounds of Formula I having antiproliferative activity.

According to one embodiment of this aspect of the invention, there is provided, a compound according to Formula IA (i.e. a compound of Formula I wherein X is CH and n is 0), or a salt thereof:

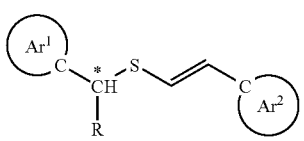

IA wherein:

$Ar^1$ and $Ar^2$ are independently selected from substituted aryl and substituted or unsubstituted heteroaryl;

R is —H or —($C_1$-$C_8$)hydrocarbyl;

*indicates that, when R is other than —H, the configuration of the substituents on the carbon atom of X is (R)—, (S)— or any mixture of (R)— and (S)—.

Preferred intermediates according to Formula IA include those wherein substituents on substituted aryl or heteroaryl $Ar^1$ are independently selected from the group consisting of halogen, —($C_1$-$C_8$)hydrocarbyl, —C(=O)$R^2$, —$NR^2_2$, —NHC(=O)$R^3$, —$NHSO_2R^3$, —NH($C_2$-$C_6$)alkylene-C(=O)$R^6$, —$NHCR^2R^4$C(=O)$R^6$, —C(=O)$OR^2$, —C(=O)$NR^2_2$, —$NO_2$, —$OR^2$, —OC(=O)$R^3$, —$OSO_2R^3$, —O 2-$C_6$)alkylene-C(=O)$R^6$, —$OCR^2R^4$C(=O)$R^6$, —P(=O)($OR^2$)$_2$, —OP(=O)($OR^2$)$_2$, —O($C_2$-$C_6$)alkylene-N(($C_1$-$C_3$)alkyl)$_2$, —NHC(=NH)$NHR^2$, —($C_1$-$C_6$)haloalkyl, —O($C_1$-$C_6$)haloalkyl and —N=CH—$R^7$; and substituents on substituted aryl or substituted heteroaryl $Ar^2$ are independently selected from the group consisting of —($C_1$-$C_8$)hydrocarbyl, —C(=O)$R^2$, halogen, —$NO_2$, —C≡N, —$OR^2$, —C(=O)$OR^2$, —$NR^2_2$, —($C_1$-$C_6$)haloalkyl and —O($C_1$-$C_6$)haloalkyl; wherein each $R^2$ is independently selected from the group consisting of —H and —($C_1$-$C_8$)hydrocarbyl;

each $R^3$ is independently selected from the group consisting of: —($C_1$-$C_8$)hydrocarbyl, —O($C_1$-$C_8$)hydrocarbyl, substituted and unsubstituted aryl, substituted and unsubstituted heterocyclyl($C_1$-$C_3$)alkyl, substituted and unsubstituted heteroaryl($C_1$-$C_3$)alkyl, —($C_2$-$C_{10}$)heteroalkyl, —($C_1$-$C_6$)haloalkyl, —$CR^2R^4NHR^5$, —$NR^2_2$, —($C_1$-$C_3$)alkyleneNH$_2$, —($C_1$-$C_3$)alkylene-N(($C_1$-$C_3$)alkyl)$_2$, —($C_1$-$C_3$)perfluoroalkylene-N(($C_1$-$C_3$)alkyl)$_2$, —($C_1$-$C_3$)alkylene-$N^+$(($C_1$-$C_3$)alkyl)$_3$, —($C_1$-$C_3$)alkylene-$N^+$($CH_2CH_2OH$)$_3$, —($C_1$-$C_3$)alkylene-$OR^2$, —($C_1$-$C_4$)alkylene-$CO_2R^2$, —($C_1$-$C_4$)alkylene-C(=O)halogen, halo($C_1$-$C_3$)alkyl-, —($C_1$-$C_3$)alkylene-C(=O)($C_1$-$C_3$)alkyl, and —($C_1$-$C_4$)perfluoroalkylene-$CO_2R^2$;

each $R^4$ is independently selected from the group consisting of —H, —($C_1$-$C_6$)alkyl, —($CH_2$)$_3$—NH—C($NH_2$)(=NH), —$CH_2$C(=O)$NH_2$, —$CH_2CO_2R^2$, —$CH_2SH$, —($CH_2$)$_2$C(=O)—$NH_2$, —($CH_2$)$_2CO_2R^2$, —$CH_2$-(2-imidazolyl), —($CH_2$)$_4$—$NH_2$, —($CH_2$)$_2$—S—$CH_3$, phenyl, —$CH_2$-phenyl, —$CH_2$—OH, —CH(OH)—$CH_3$, —$CH_2$-(3-indolyl), and —$CH_2$-(4-hydroxyphenyl);

each $R^5$ is independently selected from the group consisting of —H, —C(=O)($C_1$-$C_7$)hydrocarbyl and a carboxy terminally-linked peptidyl residue containing from 1 to 3 amino acids in which the terminal amino group of the peptidyl residue is present as a functional group selected from the group consisting of —$NH_2$, —NHC(=O)($C_1$-$C_6$)alkyl, —NH($C_1$-$C_6$)alkyl, —N(($C_1$-$C_6$)alkyl)$_2$ and —NHC(=O)O($C_1$-$C_7$)hydrocarbyl;

each $R^6$ is independently selected from the group consisting of —$OR^2$, —$NR^2_2$, and an amino terminally-linked peptidyl residue containing from 1 to 3 amino acids in which the terminal carboxyl group of the peptidyl residue is present as a functional group selected from the group consisting of —$CO_2R^2$ and —C(=O)$NR^2_2$; and each $R^7$ is independently selected from the group consisting of substituted and unsubstituted aryl and substituted and unsubstituted heteroaryl;

provided that the highest number of substituents on $Ar^1$ and $Ar^2$ is equal to the number of substitutable hydrogen atoms in the ring to which the substituents are attached.

Substituents on substituted aryl or heteroaryl groups that comprise $R^3$ or $R^7$ are preferably independently selected from the group consisting of —(C$_1$-C$_6$)alkyl, —(C$_1$-C$_6$)alkoxy, halogen, —C(═O)(C$_1$-C$_6$)alkyl, —NH$_2$, —NH(C$_1$-C$_6$)alkyl, —N((C$_1$-C$_6$)alkyl)$_2$, —NHC(═O)(C$_1$-C$_6$)alkyl, —NO$_2$, (C$_1$-C$_6$)haloalkyl, —(C$_1$-C$_6$)alkylene-NH$_2$, —CO$_2$H, CONH$_2$, C(═NH)NH$_2$, and heterocyclyl(C$_1$-C$_6$)alkyl; wherein heterocyclyl rings comprising heterocyclyl (C$_1$-C$_6$)alkyl are optionally substituted by —(C$_1$-C$_6$)alkyl or C(═O)(C$_1$-C$_6$)alkyl.

Substituents on substituted heterocyclyl groups that comprise R$^3$ are preferably independently selected from the group consisting of —(C$_1$-C$_6$)alkyl, —(C$_1$-C$_6$)alkoxy, halogen, —C(═O)(C$_1$-C$_6$)alkyl, —CO$_2$H, and CONH$_2$.

More preferably, for intermediates according to Formula IA, substituents on Ar$^1$ are selected from the group consisting of —OR$^2$, —NR$^2_2$, and —NH—CR$^2$R$^4$—C(═O)R$^6$; and substituents on Ar$^2$ are selected from the group consisting of —OR$^2$.

Preferably, for intermediates according to Formula IA, one of Ar$^1$ and Ar$^2$ is substituted phenyl. More preferably, for intermediates according to Formula IA, both Ar$^1$ and Ar$^2$ are substituted phenyl.

Other intermediates of Formula IA, are those wherein the aryl and heteroaryl groups comprising Ar$^2$ and Ar$^2$ are mono-, di- or tri-substituted. In other embodiments, the aryl and heteroaryl groups comprising Ar$^1$ and Ar$^2$ are substituted at all substitutable positions. According to some preferred embodiments, Ar$^1$ is substituted at the 3- and 4-positions. According to some preferred embodiments, Ar$^2$ is substituted at the 2- and 6-positions. According to other preferred embodiments, Ar$^2$ is substituted at the 2-, 4- and 6-positions.

In the compounds of formula IA, R is preferably —H or —(C$_1$-C$_8$)alkyl, more preferably —H or —(C$_1$-C$_6$)alkyl, most preferably —H; R$^2$ is preferably —H or —(C$_1$-C$_3$)alkyl, more preferably —H or —CH$_3$, most preferably —H; R$^4$ is preferably —H, phenyl or —(C$_1$-C$_6$)alkyl; more preferably —H, phenyl or —(C$_1$-C$_3$)alkyl, most preferably —H, —CH$_3$ or phenyl; and R$^6$ is preferably —OR$^2$.

Preferred compounds according to Formula IA include: (E)-5-((2,4,6-trimethoxystyrylthio)methyl)-2-methoxyphenol; (E)-2-(5-((2,4,6-trimethoxystyrylthio)-methyl)-2-methoxyphenylamino)propanoic acid; (E)-5-((2,4,6-trimethoxystyryl-thio)methyl)-2-methoxybenzenamine; (E)-2-(5-((2,4,6-trimethoxystyrylthio)methyl)-2-methoxyphenylamino) acetic acid; (E)-(4-fluorostyryl)(benzyl)sulfane; (E)-(4-iodostyryl)(benzyl)sulfane; (E)-(4-chlorostyryl)(benzyl)sulfane; (E)-(4-chlorostyryl)(4-methoxybenzyl)sulfane; (E)-(4-methoxybenzyl)(styryl)sulfane; (E)-(4-methoxybenzyl)(4-methoxystyryl)sulfane; (E)-(4-chlorobenzyl)(4-chlorostyryl)sulfane; (E)-(4-chlorobenzyl)(4-fluorostyryl)sulfane; (E)-(4-bromostyryl)(4-chlorobenzyl)-sulfane; and (E)-2-(5-((2,4,6-trimethoxystyrylthio)methyl)-2-methoxyphenylamino)-2-phenylacetic acid; and salts thereof.

According to another embodiment of this aspect of the invention, there is provided a compound according to Formula III, or a salt thereof:

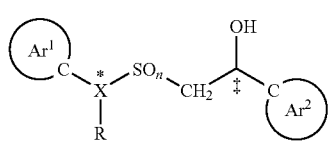

III wherein:
Ar$^1$ and Ar$^2$ are independently selected from substituted and unsubstituted aryl and substituted and unsubstituted heteroaryl;
X is N or CH;
n is 0, 1 or 2;
R is —H or —(C$_1$-C$_8$)hydrocarbyl;
* indicates that, when X is CH, and R is other than —H, the configuration of the substituents on the carbon atom of X is (R)—, (S)— or any mixture of (R)— and (S)—; and
‡ indicates that the configuration of the substituents on the designated carbon atom is (R)—, (S)— or any mixture of (R)— and (S)—;
provided that:
when X is N, then n is 2;
when X is N and Ar$^1$ is unsubstituted phenyl, then Ar$^1$ is substituted by other than —OH, —(C$_1$-C$_6$)alkyl, —NH$_2$ or —N((C$_1$-C$_6$)alkyl)$_2$; and
when Ar$^2$ is unsubstituted phenyl, then Ar$^1$ is other than 4-(C$_1$-C$_6$)alkoxyphenyl.

Preferred substituents on substituted aryl or heteroaryl Ar$^1$ and Ar$^2$ are as defined herein for compounds according to Formula I.

In some preferred embodiments of compounds according to Formula III, Ar$^1$ is substituted or unsubstituted phenyl, more preferably substituted phenyl. In other preferred embodiments, Ar$^1$ is substituted or unsubstituted phenyl, more preferably substituted phenyl. In still other preferred embodiments, both Ar$^1$ and Ar$^2$ are substituted or unsubstituted phenyl, more preferably substituted phenyl.

Preferred compounds according to Formula III, include: 5-((2-hydroxy-2-(2,4,6-trimethoxyphenyl)ethylsulfonyl)methyl)-2-methoxyphenol 2-(5-((2-hydroxy-2-(2,4,6-trimethoxyphenyl)ethylsulfonyl)methyl)-2-methoxyphenylamino)propanoic acid; 2-(3-amino-4-methoxybenzylsulfonyl)-1-(2,4,6-trimethoxyphenyl) ethanol; 2-(5-((2-hydroxy-2-(2,4,6-trimethoxyphenyl) ethylsulfonyl)methyl)-2-methoxyphenylamino)acetic acid; 2-(benzylsulfonyl)-1-(4-fluorophenyl)ethanol; 2-(benzylsulfonyl)-1-(4-chlorophenyl)ethanol; 2-(benzylsulfonyl)-1-(4-iodophenyl)ethanol; 2-(4-methoxybenzylsulfonyl)-1-(4-chlorophenyl)ethanol; 2-(4-methoxy-benzylsulfonyl)-1-phenylethanol; 2-(4-methoxybenzylsulfonyl)-1-(4-methoxyphenyl)ethanol; 2-(4-chlorobenzylsulfonyl)-1-(4-chlorophenyl)ethanol; 2-(4-chlorobenzylsulfonyl)-1-(4-fluoro-phenyl)ethanol; 2-(4-chlorobenzylsulfonyl)-1-(4-bromophenyl)ethanol; 2-(5-((2-hydroxy-2-(2,4,6-trimethoxyphenyl)ethylsulfonyl)methyl)-2-methoxyphenylamino)-2-phenylacetic acid; 5-((2-hydroxy-2-(2,4,6-trimethoxyphenyl)ethylsulfinyl)methyl)-2-methoxyphenol; 2-(5-((2-hydroxy-2-(2,4,6-trimethoxyphenyl)ethylsulfinyl)methyl)-2-methoxyphenylamino)propanoic acid; 2-(3-amino-4-methoxybenzylsulfinyl)-1-(2,4,6-trimethoxyphenyl)ethanol; 2-(5-((-2-hydroxy-2-(2,4,6-trimethoxyphenyl)ethylsulfinyl) methyl)-2-methoxyphenylamino)acetic acid; 2-(benzylsulfinyl)-1-(4-fluorophenyl)ethanol; 2-(benzylsulfinyl)-1-(4-chlorophenyl)ethanol; 2-(benzylsulfinyl)-1-(4-iodophenyl)ethanol; 2-(4-methoxybenzylsulfinyl)-1-(4-chlorophenyl)-ethanol; 2-(4-methoxybenzylsulfinyl)-1-phenylethanol; 2-(4-methoxybenzylsulfinyl)-1-(4-methoxyphenyl)ethanol; 2-(4-chlorobenzylsulfinyl)-1-(4-chlorophenyl)ethanol; 2-(4-chloro-benzylsulfinyl)-1-(4-fluorophenyl)ethanol; 2-(4-chlorobenzylsulfinyl)-1-(4-bromophenyl)-ethanol; 2-(2-hydroxy-2-(2,4,6-trimethoxyphenyl)ethylsulfinyl)methyl)-2-methoxyphenyl-amino)-2-phenylacetic acid; 5-((2-hydroxy-2-(2,4,6-trimethoxyphenyl)ethylthio)methyl)-2- methoxyphenol; 2-(5-((2-hydroxy-2-(2,4,6-trimethoxyphenyl)ethylthio)methyl)-2-methoxyphenylamino)propanoic acid; 2-(3-amino-4-methoxybenzylthio)-1-(2,4,6-trimethoxy-phenyl)ethanol; 2-(5-((-2-hydroxy-2-(2,4,6-trimethoxyphenyl)ethylthio)methyl)-2-methoxyphenylamino)acetic acid; 2-(benzylthio)-1-(4-fluorophenyl)ethanol; 2-(benzylthio)-1-(4-chlorophenyl)ethanol; 2-(benzylthio)-1-(4-iodophenyl)ethanol; 2-(4-methoxybenzylthio)-1-(4-chlorophenyl)ethanol; 2-(4-methoxybenzylthio)-1-phenylethanol; 2-(4-methoxybenzylthio)-1-(4-methoxyphenyl)ethanol; 2-(4-chlorobenzylthio)-1-(4-chlorophenyl)ethanol; 2-(4-chlorobenzyl-thio)-1-(4-fluorophenyl)ethanol; 2-(4-chlorobenzylthio)-1-(4-bromophenyl)ethanol; 2-(5-((2-hydroxy-2-(2,4,6-trimethoxyphenyl)ethylthio)methyl)-2-methoxyphenylamino)-2-phenylacetic acid; 5-(2-hydroxy-2-(2,4,6-trimethoxyphenyl)ethylsulfonylamino)-2-methoxyphenol 2-(5-((2-hydroxy-2-(2,4,6-trimethoxyphenyl)ethylsulfonyl)methyl)-2-methoxyphenylamino)propanoic acid; 2-(3-amino-4-methoxybenzylsulfonyl)-1-(2,4,6-trimethoxyphenyl)ethanol; 2-(5-(((-2-hydroxy-2-(2,4,6-trimethoxyphenyl)ethylsulfonyl)methyl)-2-methoxyphenylamino)acetic acid; 2-(benzylsulfonyl)-1-(4-fluorophenyl)ethanol; 2-(4-methoxybenzylsulfonyl)-1-(4-chlorophenyl)ethanol; 2-(benzylsulfonyl)-1-(4-iodophenyl)ethanol; 2-(benzylsulfonyl)-1-(4-chlorophenyl)ethanol; 2-(4-chlorobenzylsulfonyl)-1-(4-chlorophenyl)ethanol; 2-(4-methoxybenzylsulfonyl)-1-phenylethanol; 2-(4-chlorobenzylsulfonyl)-1-(4-fluorophenyl)ethanol; 2-(4-chlorobenzylsulfonyl)-1-(4-bromophenyl)ethanol; 2-(5-((2-hydroxy-2-(2,4,6-trimethoxyphenyl)ethyl sulfonyl)methyl)-2-methoxyphenylamino)-2-phenyl acetic acid; and salts thereof.

According to some sub-embodiments of compounds according to Formula III, the configuration of the substituents on the carbon atom designated by ‡ is (R)—, and the compound is substantially free of the corresponding (S)-enantiomer of the same compound; or is (S)—, and the compound is substantially free of the corresponding (R)-enantiomer of the same compound.

According to one sub-embodiment of the compounds according to Formula III, the compound comprises an (R)-enantiomer with respect to the absolute configuration at the carbon designated by ‡, and is substantially free of the corresponding (S)-enantiomer of the same compound.

According to another sub-embodiment of the compounds according to Formula III, the compound comprises an (S)-enantiomer with respect to the absolute configuration at the carbon designated by ‡, and is substantially free of the corresponding (R)-enantiomer of the same compound.

DEFINITIONS

Where examples are given in the definitions that follow, the examples are intended to be illustrative and not limiting.

The term "alkyl", by itself or as part of another substituent means, unless otherwise stated, a straight, branched or cyclic chain saturated hydrocarbon radical, including di- and multi-radicals, having the number of carbon atoms designated in an expression such as $(C_x-C_y)$alkyl. The expression "$(C_x-C_y)$alkyl" wherein x<y, represents an alkyl chain containing a minimum of x carbon atoms and a maximum of y carbon atoms. Examples include: methyl, ethyl, propyl, isopropyl, butyl, isobutyl, t-butyl, pentyl, neopentyl, hexyl, cyclohexyl and cyclopropylmethyl. Preferred is $(C_1-C_3)$alkyl, particularly ethyl, methyl and isopropyl.

The term "cycloalkyl" refers to alkyl groups that contain at least one cyclic structure. Examples include cyclohexyl, cyclopentyl, norbornyl, adamantyl and cyclopropylmethyl. Preferred is $(C_3-C_{12})$cycloalkyl, particularly cyclopentyl, norbornyl, and adamantyl.

The term "alkylene" refers to a divalent alkyl radical having the number of carbon atoms designated, i.e. $(C_1-C_6)$ means —$CH_2$—; —$CH_2CH_2$—; —$CH_2CH_2CH_2$—; —$CH_2CH_2CH_2CH_2$—; —$CH_2CH_2CH_2CH_2CH_2$—; and —$CH_2CH_2CH_2CH_2CH_2CH_2$—, and also includes branched divalent structures such as, for example, —$CH_2CH(CH_3)CH_2CH_2$— and —$CH(CH_3)CH(CH_3)$—, and divalent cyclic structures such as, for example 1,3-cyclopentyl.

The term "arylene", by itself or as part of another substituent means, unless otherwise stated, a divalent aryl radical. Preferred are divalent phenyl radicals, or "phenylene" groups, particularly 1,4-divalent phenyl radicals.

The term "heteroarylene", by itself or as part of another substituent means, unless otherwise stated, a divalent heteroaryl radical. Preferred are five- or six-membered monocyclic heteroarylene. More preferred are heteroarylene moieties comprising divalent heteroaryl rings selected from the group consisting of pyridine, piperazine, pyrimidine, pyrazine, furan, thiophene, pyrrole, thiazole, imidazole and oxazole, such as, for example 2,5-divalent pyrrole, thiophene, furan, thiazole, oxazole, and imidazole.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are $(C_1-C_6)$alkoxy, particularly ethoxy and methoxy.

The carbon chains in the alkyl and alkoxy groups which may occur in the compounds of the invention may be cyclic, straight or branched, with straight chain being preferred. The expression "$(C_1-C_6)$alkyl" thus extends to alkyl groups containing one, two, three, four, five or six carbons. The expression "$(C_1-C_6)$alkoxy" thus extends to alkoxy groups containing one, two, three, four, five or six carbons.

The term "hydrocarbyl" refers to any moiety comprising only hydrogen and carbon atoms. The term includes, for example, alkyl, alkenyl, alkynyl, aryl and benzyl groups. Preferred are $(C_1-C_7)$hydrocarbyl. More preferred are $(C_1-C_6)$alkyl and $(C_3-C_{12})$cycloalkyl.

The term "heteroalkyl" by itself or in combination with another term means, unless otherwise stated, a stable straight or branched chain radical consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

The terms "halo" or "halogen" by themselves or as part of another substituent mean, unless otherwise stated, a fluorine, chlorine, bromine, or iodine atom.

The term "aromatic" refers to a carbocycle or heterocycle having one or more polyunsaturated rings having aromatic character (4n+2) delocalized π (pi) electrons. The term "aromatic" is intended to include not only ring systems containing only carbon ring atoms but also systems containing one or more non-carbon atoms as ring atoms. Systems containing one or more non-carbon atoms may be known as "heteroaryl" or "heteroaromatic" systems. The term "aromatic" thus is deemed to include "aryl" and "heteroaryl" ring systems.

The expression "electrophilic acylation" refers to an electrophilic aromatic substitution reaction wherein the electrophilic reagent is a carbonyl compound such as, for example, a carboxylic acid, a carboxylic acid halide are an acid anhydride. The electrophilic acylation is generally a "Friedel Crafts" acylation. A Friedel Crafts acylation may be catalyzed by a Lewis Acid or by a mineral acid.

The expression "Lewis acid" refers to a substance that acts as an electron-pair acceptor. Examples include, but are not limited to, $AlCl_3$, $BF_3$, $BCl_3$, $SnCl_2$, $ZnBr_2$, $ZnCl_2$, $Al(C_1-C_6$ alkyl$)_3$, $AlCl(C_1-C_6$ alkyl$)_2$, and $AlCl_2(C_1-C_6$ alkyl).

The expression "leaving group" refers to an atom, or a group of atoms, that is displaced from a molecule as stable species during a chemical reaction, particularly a nucleophilic displacement reaction. The leaving group takes with it the bonding electrons from the bond connecting the leaving group to the molecule from which it is displaced. The leaving group is generally an anion, e.g. $Cl^-$ or $CH_3SO_3^-$.

A "mineral acid" is generally a strong acid such as, for example, HCl, HBr, $H_2SO_4$, or $HNO_3$.

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl which may be substituted or unsubstituted. The aforementioned listing of aryl moieties is intended to be representative, not limiting.

The term "heterocycle" or "heterocyclyl" or "heterocyclic" by itself or as part of another substituent means, unless otherwise stated, an unsubstituted or substituted, stable, monocyclic or polycyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

Heterocyclyl groups are inclusive of monocyclic and polycyclic heteroaryl groups and monocyclic and polycyclic groups that are not aromatic, such as saturated and partially saturated and monocyclic and polycyclic partially saturated monocyclic and polycyclic groups.

The term "heteroaryl" or "heteroaromatic" refers to a heterocycle having aromatic character, and includes both monocyclic heteroaryl groups and polycyclic heteroaryl groups. A polycyclic heteroaryl group may include one or more rings which are partially saturated.

Examples of monocyclic heteroaryl groups include: pyridyl; pyrazinyl; pyrimidinyl, particularly 2- and 5-pyrimidinyl; pyridazinyl; thienyl; furyl; pyrrolyl, particularly 2-pyrrolyl and 1-alkyl-2-pyrrolyl; imidazolyl, particularly 2-imidazolyl; thiazolyl, particularly 2-thiazolyl; oxazolyl, particularly 2-oxazolyl; pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl; and 1,3,4-oxadiazolyl.

Examples of monocyclic heterocycles that are not aromatic include saturated monocyclic groups such as: aziridine, oxirane, thiirane, azetidine, oxetane, thietane, pyrrolidine, pyrroline, imidazoline, pyrazolidine, dioxolane, 1,4-dioxane, 1,3-dioxane, sulfolane, tetrahydrofuran, thiophane, piperazine, morpholine, thiomorpholine, tetrahydropyran, homopiperazine, homopiperidine, 1,3-dioxepane, hexamethyleneoxide and piperidine; and partially saturated monocyclic groups such as: 1,2,3,6-tetrahydropyridine, 1,4-dihydropyridine, 2,3-dihydrofuran, 2,5-dihydrofuran, 2,3-dihydropyran, 1,2-dihydrothiazole, 1,2-dihydrooxazole, 1,2-dihydroimidazole and 4,7-dihydro-1,3-dioxepin.

Examples of polycyclic heteroaryl groups include: indolyl, particularly 3-, 4-, 5-, 6- and 7-indolyl, quinolyl, isoquinolyl, particularly 1- and 5-isoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarin, benzofuryl, particularly 3-, 4-, 1,5-naphthyridinyl, 5-, 6- and 7-benzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, tetrahydroquinolyl; 1,2,3,4-tetrahydroisoquinolyl; dihydrocoumarinyl; 2,3-dihydrobenzofuryl; 2,3-dihydrobenzothienyl, N-methyl-2-indolinyl; and indolinyl.

Examples of non-aromatic polycyclic heterocycles include: pyrrolizidinyl and quinolizidinyl.

The aforementioned listing of non-aromatic heterocyclic moieties and heteroaryl moieties is intended to be representative, not limiting.

Preferred heteroaryl groups are 2-, 3- and 4-pyridyl; pyrazinyl; 2- and 5-pyrimidinyl; 3-pyridazinyl; 2- and 3-thienyl; 2- and 3-furyl; pyrrolyl; particularly N-methylpyrrol-2-yl; 2-imidazolyl; 2-thiazolyl; 2-oxazolyl; pyrazolyl; particularly 3- and 5-pyrazolyl; isothiazolyl; 1,2,3-triazolyl; 1,2,4-triazolyl; 1,3,4-triazolyl; tetrazolyl, 1,2,3-thiadiazolyl; 1,2,3-oxadiazolyl; 1,3,4-thiadiazolyl and 1,3,4-oxadiazolyl; indolyl, particularly 2-, 3-, 4-, 5-, 6- and 7-indolyl; cinnolinyl; quinoxalinyl, particularly 2- and 5-quinoxalinyl; quinazolinyl, particularly 2-, 5-, 6-, 7- and 8-quinazolinyl; phthalazinyl; 1,8-naphthyridinyl; 1,5-naphthyridinyl, particularly 1,5-naphthyridin-3-yl and 1,5-naphthyridin-4-yl; 1,4-benzodioxanyl; coumarinyl; benzofuryl, particularly 2-, 3- 5-, b- and 7-benzofuryl; 1,2-benzisoxazolyl; benzothienyl, particularly 2-, 3-, 4-, 5-, 6-, and 7-benzothienyl; benzoxazolyl; benzthiazolyl, particularly 2-benzothiazolyl and 5-benzothiazolyl; purinyl; benzimidazolyl, particularly 2-benzimidazolyl; benztriazolyl; thioxanthinyl; carbazolyl; carbolinyl; and acridinyl, particularly 6-acridinyl.

More preferred heteroaryl groups are 2,3- and 4-pyridyl; 2- and 3-thienyl; 2- and 3-furyl; 2-pyrrolyl; 2-imidazolyl; 2-thiazolyl; 2-oxazolyl; 2- and 3-indolyl; 2-, and 3-benzofuryl; 3-(1,2-benzisoxazolyl); 2-, and 3-benzothienyl; 2-benzoxazolyl; 1- and 2-benzimidazolyl, 2-, 3- and 4-quinolyl; and 2- and 5-benzthiazolyl. Most preferred heteroaryl groups are 2- and 3-indolyl; 2- and 3-pyrrolyl, 2-, and 3-benzofuryl; and 2-, and 3-benzothienyl.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

The α,β-unsaturated sulfides, sulfones, sulfoxides and sulfonamides are characterized by isomerism resulting from the presence of a double bond. This isomerism is commonly referred to as cis-trans isomerism, but the more comprehensive naming convention employs E and Z designations. The compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4th ed., 1992, p. 127-138. Using this system of nomenclature, the four groups about a double bond are prioritized according to a series of rules. Then, that isomer with the two higher ranking groups on the same side of the double bond is designated Z (for the German word "zusammen", meaning together). The other isomer, in which the two higher-ranking groups are on opposite sides of the double bond, is designated E (for the German word "entgegen", which means "opposite"). Thus if the four groups on a carbon-carbon double bond are ranked with A being the lowest rank and D being highest, A>B>C>D, the isomers would be named as in Scheme 1.

Scheme 1

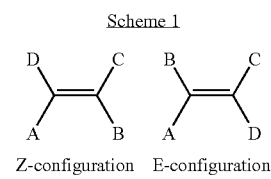

Z-configuration  E-configuration

α,β-Unsaturated (aryl or heteroaryl) sulfides, sulfones, sulfoxides and sulfonamides in the E-configuration are formed selectively the process of the present invention.

Some of the sulfides, sulfones, sulfoxides and sulfonamides according to Formulae I and III may be characterized by isomerism resulting from the presence of a chiral center at X, when X is CH and R is other than —H. Compounds according to Formula III have a chiral center at the carbon designated by ‡. The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. See March, *Advanced Organic Chemistry*, 4th Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example shown in Scheme 2 below, the Cahn-Ingold-Prelog ranking is A>B>C>D. The lowest ranking atom, D is oriented away from the viewer.

Scheme 2

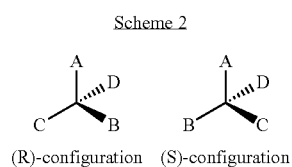

(R)-configuration  (S)-configuration

Unless otherwise indicated, both absolute configurations and mixtures thereof are included in the scope of α,β-unsaturated (aryl or heteroaryl) sulfides, sulfones, sulfoxides and sulfonamides of Formula I that may be prepared according to the process of the invention and novel compounds of Formula M.

The expression "substantially free" of the (R)- or (S)-enantiomer, when used to refer to an optically active compound according to Formula III, means the (R)- and (S)-enantiomers of the compound have been separated such that the composition is 80% or more by weight a single enantiomer. Preferably, the composition is 90% or more by weight a single enantiomer. More preferably, the composition is 95% or more by weight a single enantiomer. Most preferably, the composition is 99% or more by weight a single enantiomer.

Thus, by an "(R)-enantiomer of a compound according to Formula III substantially free of the (S)-enantiomer" is meant the compound comprises 80% or more by weight of its (R)-enantiomer and likewise contains 20% or less of its (S)-enantiomer as a contaminant, by weight.

Isolated optical isomers may be purified from racemic mixtures by well-known chiral separation techniques. According to one such method, a racemic mixture of a compound having the structure of Formula I, or a chiral intermediate thereof, is separated into 99% wt. pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

In addition, chiral compounds such as the secondary alcohols according to Formula III may be prepared by chiral reduction of intermediate ketone compounds according to Formula II. Catalytic asymmetric synthesis using chiral metal complexes as catalyst precursors has been employed successfully to reduce prochiral ketones to optically active secondary alcohols. See, Noyori R., *Asymmetric Catalysis in Organic Synthesis*, New York, John Wiley, 1994, pages 1-82, the entire disclosure of which is incorporated herein by reference.

For compounds according to Formula III, more than one chiral center may be present in a molecule, i.e., the carbon atom of X when X is CH and R is other than —H, and the carbon atom designated by ‡. Two pairs of enantiomers result from the presence of two chiral centers. Only the relationship between the mirror-image isomers is termed enantiomeric. The relationship between a single enantiomer and other isomers that exist as a result of additional chiral centers is termed "diastereomeric." Diastereomeric pairs may be resolved by known separation techniques including normal and reverse phase chromatography, and crystallization. Compounds of the present invention according to Formula III, wherein X is CH and R is other than —H, encompass isolated diastereomers, e.g., (R,R), (R,S), (S,R), and (S,S); isolated diastereomeric pairs, e.g., (R,R) and (R,S), or (S,R) and (S,S); and all mixtures of diastereomers in any proportion.

Nomenclature employed herein for providing systematic names for compounds disclosed herein may be derived using the computer program package, CHEMDRAW®, CambridgeSoft Corporation, Cambridge, Mass. 02140.

DETAILED DESCRIPTION OF THE INVENTION

Preparation of the Compounds of Formula I by the Process of the Present invention comprises reduction of a β-ketosulfide, β-ketosulfoxide, β-ketosulfone, or β-ketosulfonamide compound of Formula II to form a secondary alcohol of Formula III. This step is followed by dehydration of the alcohol of Formula III to form a compound according to Formula I.

A. Reduction of Compounds According to Formula II

Reducing a compound of Formula II to yield a secondary alcohol of Formula III may be performed by reacting the Formula II compound with a suitable reducing agent under reaction conditions capable of selectively reducing a ketone to the corresponding alcohol. The reducing agent and reaction conditions may further be selected to reduce other moieties present in the Formula II compound II the reduction of such additional moieties serves to allow the preparation of a specific desired compound of Formula I.

Suitable reducing agents include hydride reagents such as sodium borohydride, lithium aluminum hydride and sodium bis(2-methoxyethoxy)aluminum hydride. The reaction is preferably performed in the presence of a solvent. Suitable solvents include organic solvents such as, for example diethyl ether, t-butylmethyl ether, tetrahydrofuran (THF) and toluene. The reaction is preferably performed at a temperature in the range from about 0° C. to about 100° C., more preferably from about 0° C. to about 50° C., most preferably from about 0° C. to about 30° C.

The desired compound according to Formula II may be isolated from the reaction mixture by, for example, adding a suitable proton source, e.g., water, acetic acid, aqueous HCl, or aqueous $NH_4^+Cl$ to the reaction mixture to quench any remaining hydride reagent, hydrolyzing intermediate metal species, removing the volatile components of the reaction mixture under vacuum and purifying the residue, e.g., by chromatographic separation.

Suitable conditions for reducing a compound of Formula II to yield a secondary alcohol of Formula III also include catalytic hydrogenation conditions. Suitable catalysts, for catalytic hydrogenation include platinum palladium, ruthenium and nickel reagents. The reaction is preferably performed in the presence of a suitable solvent. Suitable solvents include alkyl alcohols such as methanol and ethanol, THF, and dioxane. The reaction is preferably performed at a hydrogen pressure in the range from about 1 to about 5 atmospheres, more preferably from 1 to 3 atmospheres. The reaction is preferably performed at a temperature in the range from about 0° C. to about 50° C., most preferably in the range form about 20° C. to about 30° C. The desired compound according to Formula II may be isolated from the reaction mixture by, for example, removing the catalyst, preferably by filtration, concentrating the filtered reaction mixture to form a residue, and purifying the residue, e.g., by chromatographic separation.

Exemplary reaction conditions for performing catalytic hydrogenation are described by R. L. Augustine, *Catalytic Hydrogenation*, Marcel Dekker, Inc., New York (1965), and Paul N. Rylander, *Catalytic Hydrogenation in Organic Synthesis*, Academic Press, New York (1979) and the references cited therein, the entire disclosures of which are incorporated herein by reference.

The reduction of a compound of Formula II to yield an optically active secondary alcohol of Formula III may be performed by using any reducing agent and reaction conditions capable of asymmetrically reducing a ketone to the corresponding optically active alcohol. Suitable reactions include, for example, catalytic hydrogenation with a chiral Rh(I), Ir(I), Ru(II), or lanthanoid complex as a catalyst precursor; hydrogen; and a chiral auxiliary and enantioselective hydroboration with reagents such as, for example, (+)-B-chlorodiisopinocampheylborane or (−)-B-chlorodiisopinocampheylborane.

Suitable chiral auxiliaries for chiral catalytic reductions include, for example, BINAP (2,2'-bis-(diphenylphosphino)-1,1'-binaphthyl) or an analog thereof, and PNP (6-diphenylphosphinomethyl)-pyridine Preferred hydrogenation catalysts include, for example, Ru-(R)BINAP(Br)$_2$, Ru-(R)BINAP(Cl)$_2$, Ru-(S)BINAP(Br)$_2$, Ru-(S)BINAP(Cl)$_2$, Ru-(R)BINAP(OAc)$_2$, and Ru-(S)BINAP(OAc)$_2$. A suitable hydrogen pressure for the asymmetric reduction is preferably in the range from about 1 to about 100 atmospheres, more preferably from about 1 to about 70 atmospheres. The reaction is preferably performed at a temperature in the range from about 0° C. to about 50° C., more preferably from about 20° C. to about 30° C.

B. Dehydration of Compounds According to Formula III

Dehydrating a compound of Formula Di to yield an α,β-unsaturated sulfone, sulfoxide or sulfonamide of Formula I may be performed by reaction with a suitable dehydrating agent under conditions capable of accomplishing such a dehydration.

The dehydration of the Formula III compound may be performed by reacting the Formula III compound with a Lewis acid or a mixture of different Lewis acids. Preferred Lewis acids include $BF_3$ etherate, $BCl_3$ and aluminum chloride. The reaction is preferably performed in the presence of a suitable solvent, most preferably a solvent that forms a low boiling azeotrope with water. Suitable solvents include, for example, non-protic solvents such as methyl acetate, ethyl acetate diethyl ether, THF, toluene, methylene chloride, chloroform or carbon tetrachloride.

The reaction may be carried out at a temperature in the range, for example, from about −20° C. to about 100° C., preferably in the range from about −20° C. to about 25° C., most preferably in the range from about 0° C. to about 10° C.

The desired product of Formula I may be isolated from the dehydration reaction mixture, for example, by removing the volatile components of the reaction mixture under vacuum and purifying the residue by chromatographic separation.

Dehydration of the alcohol of Formula III may also be accomplished by first derivatizing the —OH group, for example by acylation or halogenation, either prior to, or during, the dehydration reaction. The derivatized alcohol of Formula III then reacts to form the Formula I olefin by a β-elimination, e.g., dehydrohalogenation. Derivatization of the —OH group serves to replace —OH with a leaving group that is more reactive than —OH (e.g., tosyl, mesyl, trifyl, nosyl, chloro, bromo, or iodo) and thereby facilitate β-elimination of the derivatized —OH to yield the double bond. Suitable derivatizations of the —OH group of a compound of Formula III include, for example, acylation, e.g., acetylation; sulfonylation, e.g., tosylation; and halogenation, e.g. chlorination.

Acylation of the —OH group of a Formula III compound may be accomplished by reaction of the Formula III compound with an acylating agent such as an anhydride, e.g., acetic anhydride or an acid halide, e.g., acetyl chloride. The acylation reaction is preferably performed in the presence of a suitable solvent. Suitable solvents include aprotic solvents such as, for example, THF or ether.

Sulfonylation of the —OH group of a Formula III compound may be accomplished by reaction of the Formula III compound with an sulfonylating agent such as, for example, an anhydride, e.g., triflic anhydride or a sulfonic acid halide, e.g., tosyl chloride. The sulfonylation reaction is preferably performed in the presence of a suitable solvent. Suitable solvents include aprotic solvents such as, for example, THF or ether.

Halogenation of the —OH group of a Formula III compound may be accomplished by reaction of the Formula III compound with an halogenating agent such as, for example, thionyl chloride or phosphorous oxychloride. The halogenation reaction is preferably performed in the presence of a suitable solvent. Suitable solvents include aprotic solvents such as, for example, THF or ether. The halogenation reaction serves to replace the —OH group with a halogen.

Dehydration of a compound according to Formula II, or a compound of Formula II derivatized, by acylation, sulfonylation or halogenation, for example, may be accomplished by reaction with a base such as triethylamine (TEA), N,N-diisopropylethylamine (DIEA) or diazabicycloundecene (DEW). The reaction is preferably performed in the presence of a suitable solvent such as for example, methyl acetate, ethyl acetate diethyl ether, THF, toluene, methylene chloride, chloroform or carbon tetrachloride. Preferably, the reaction is performed at an elevated temperature from about 30° C. to about 100° C., more preferably at the reflux temperature of the solvent in which the reaction is conducted.

C. Preparation of Compounds According to Formula II.

One preferred method for the preparation of compounds according to Formula II is by electrophilic acylation of an aromatic compound comprising $Ar^2$, according to Scheme 3.

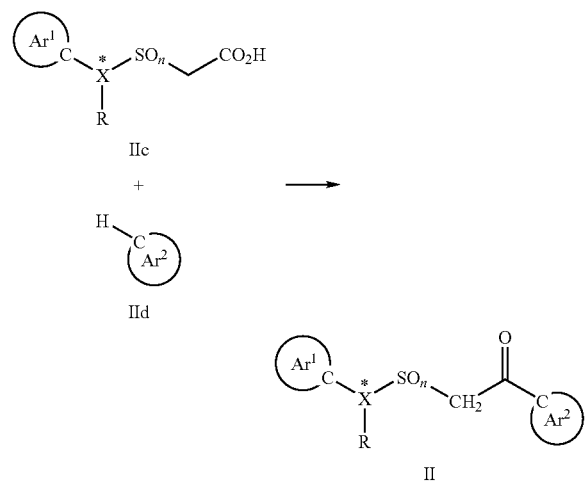

The reaction of a compound of Formula IIe and a compound of Formula IId is preferably performed, according to Scheme 3, by adding a Lewis acid to a solution of the reactant compounds, and heating the resulting reaction mixture to a suitable reaction temperature. The reaction is preferably performed at a temperature in the range from about 50° C. to about 200° C., preferably from about 80° C. to about 150° C. If the Formula IId reactant is a liquid, it may be employed as the solvent in the reaction. Compounds of Formula IId which may be employed as the solvent in the reaction include benzene, fluorobenzene, chlorobenzene and anisole. If the Formula IId reactant is not suitable as a solvent, a suitable solvent is preferably a high boiling solvent which is unreactive under the reaction conditions, e.g., nitrobenzene. Suitable Lewis acids include, for example, $AlCl_3$, $BF_3$, $BCl_3$, $ZnCl_2$, $ZnBr_2$, and $P_2O_5$.

A preferred preparation of the sulfide compounds according to Formula II proceeds, as shown in Scheme 4, by reacting an aromatic mercaptan according to Formula IIb and a Formula IIa compound, wherein $Ar^1$, $Ar^2$, R, and * are defined as for Formula I, above, and X is CH. Sulfoxide compounds of Formula II or sulfone compounds of Formula II may be prepared according to Scheme 7, by oxidizing a Formula II sulfide compound (X=CH, n=0) to the corresponding sulfoxide or sulfone according Formula II.

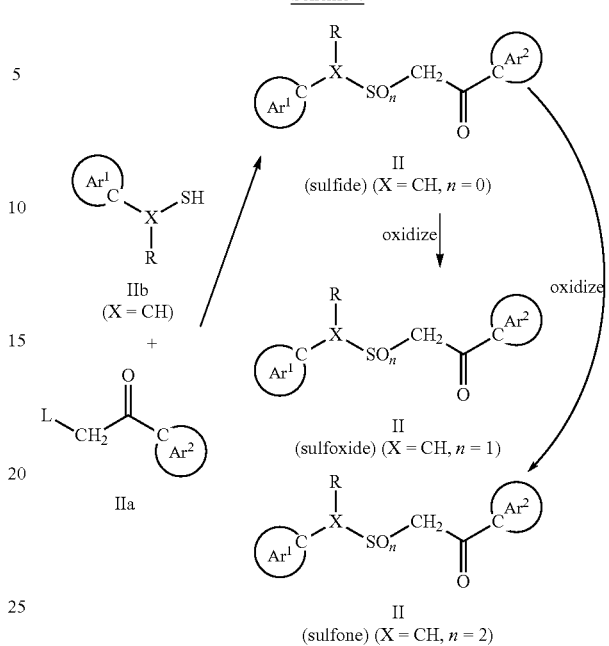

The reaction of a compound of Formula IIa and a compound of Formula IIb (X=CH), according to Scheme 4 is preferably performed by contacting the compound of Formula IIa with a base addition salt of the compound of Formula IIb (X=CH), preferably in the presence of a suitable solvent.

Preferred base addition salts of a compound of Formula IIb are alkali metal salts or alkaline earth metal salts. The salt of the compound according to Formula IIb may be prepared, for example, by contacting the compound of Formula IIb with a solution of a base, e.g. sodium hydroxide in a suitable solvent. Suitable solvents include polar organic solvents which are capable of solvating the base, preferably a low boiling alcohol such as methanol or ethanol. The amount of solvent is preferably sufficient to achieve a concentration of the Formula IIb compound in the range from about 0.1 M to about 0.3M, most preferably about 0.2M. Preferably, about one equivalent of the base is used, based on the amount of the Formula IIa compound. The formation of the salt of the Formula IIb compound is preferably performed at a temperature in the range from about 0° C. to about 50° C., more preferably from about 0° C. to about 30° C., most preferably at about 25° C.

The compound according to Formula IIa comprises a leaving group, L. Preferred leaving groups are halogens and sulfonates, e.g., tosylate or mesylate. Preferably, the Formula IIa compound is added to the Formula IIb compound in portions or continuously over a suitable time interval. Preferably, the time interval is from about 2 to about 60 minutes, more preferably from about 5 to about 30 minutes. The addition of the Formula IIa compound is preferably performed at a temperature in the range from about 0° C. to about 50° C., more preferably from about 0° C. to about 30° C., most preferably at about 25° C. When the addition is complete, the resulting reaction mixture is preferably heated to a suitable reaction temperature. A suitable temperature is preferably in the range from about 50° C. to about 100° C., most preferably at about the boiling point of the reaction mixture.

The reaction mixture is maintained at the reaction temperature until the reaction is complete. Determination of the completion of the reaction may be determined by any reasonable means. Preferably, the reaction is monitored by thin layer chromatography (TLC) or by high performance liquid chromatography (HPLC).

When the reaction is complete, the Formula II sulfide compound is preferably isolated by cooling the reaction mixture and pouring the reaction mixture onto ice or ice water to precipitate the product. The product Formula II sulfide compound may then be separated, e.g., by filtration and dried under vacuum.

Formula II sulfoxide compounds and Formula II sulfone compounds may be prepared by oxidizing the Formula II sulfide compound. Oxidation to the sulfone compound of Formula II may be accomplished by reaction with any oxidizing agent and reaction conditions capable of oxidizing a sulfide to a sulfone. Suitable oxidizing reagents for both oxidation reactions include, for example, peroxides such as, hydrogen peroxide, peracids such as meta-chloroperoxybenzoic acid (MCPBA) and persulfates such as OXONE® (potassium peroxymonosulfate). The reaction is preferably carried out in the presence of a suitable solvent. Suitable solvents include, for example, water, acetic acid or non-polar solvents such as dichloromethane (DCM).

Reaction to selectively form a Formula II sulfoxide compound is preferably performed at low temperature, more preferably from about −10° C. to about 20° C. A reaction to form the Formula II sulfoxide compound is preferably monitored so as to terminate the reaction prior to appreciable oxidation to the corresponding sulfone. When the reaction is complete, the reaction mixture may be poured onto crushed ice. A solid precipitate of the crude product may be collected by filtration and recrystallized from a suitable solvent such as, for example, hot water to yield the purified Formula II sulfoxide compound.

Reaction to form the Formula II sulfone compound may be performed at higher temperature, for example, from about 20° C. to about 100° C. with an oxidizing agent such as, for example, 30% hydrogen peroxide in glacial acetic acid. When the reaction is complete, the reaction mixture may be cooled to ambient temperature and poured onto crushed ice. A solid precipitate of the crude product may be collected by filtration and recrystallized from a suitable solvent such as, for example, hot water to yield the purified Formula II sulfone compound.

D. Use of Protecting Groups in the Preparation of Compounds of the Invention

In the reactions described herein for preparing compounds of Formula I, any reactive groups present may be protected during a reaction by protecting groups. A "protecting group" is a chemical functionality which selectively blocks one or more reactive sites in a multifunctional compound such that a chemical reaction can be carried out selectively at another unprotected reactive site. Certain processes for preparation of compounds according to the present invention may rely upon protecting groups to block reactive functional groups that are present in the reactants. Examples of reactive groups which may be blocked by suitable protecting groups include —$NH_2$ or —OH groups which may be present, for example, on chemical intermediates according to Formula IIb. If such groups were not blocked by suitable protecting groups prior to reaction with an intermediate according to Formula IIa, unwanted side reactions could occur. One example of such a side reaction is that a —$NH_2$ or —OH group on the Formula IIb compound may react with the Formula IIa intermediate in addition to, and in competition with the —SH group on the Formula IIb compound.

Thus, the protecting group may be introduced prior to carrying out a particular reaction that may affect a chemical group other than one that is desired. The protecting group is optionally removed at any suitable point in the synthesis after the reaction which required use of the protecting group.

For example, in the process of preparing a compound according to Formula I, the desired product of Formula I may have an acetyl group on $Ar^1$. If the intermediate of Formula II is substituted by an acetyl group and is reduced to form an intermediate of Formula III, the acetyl group on $Ar^1$ will be reduced in the reaction. Thus, the intermediate of Formula II would be prepared with the acetyl group protected, for example as a ketal. The ketal will be unreactive under the conditions required to reduce the intermediate of Formula I to an intermediate of Formula III.

Protecting groups may be chosen from any protecting groups described in the literature or known to the skilled chemist as suitable for the protection of the functional group which must be protected. Protecting groups may be introduced and removed by any suitable chemical synthesis method that is described in the art or known to the skilled chemist as suitable for the removal of the particular protecting group. Methods of removing protecting groups are preferably selected so as to effect selective removal of the protecting group with minimum effect on other chemical functionality in the molecule.

Protecting groups for alcoholic or phenolic hydroxyl groups, include, for example, acetates, haloalkyl carbonates, benzyl ethers, alkylsilyl ethers, heterocyclyl ethers, and methyl or alkyl ethers. Protecting groups for carboxyl groups include t-butyl, benzyl or methyl esters. Protecting groups for amine groups include benzyl, 2,4-dimethoxybenzyl, CBZ, p-methoxybenzyloxycarbonyl, p-nitrobenzyloxycarbonyl, t-BOC, trifluoroacetyl. Methods for removal of hydroxy and amino protecting groups include, for example, acid, base, metal or enzyme-catalyzed hydrolysis for CBZ; acid or iodotrimethylsilane for removal of t-BOC groups; hydrogenation for benzyl and CBZ; and photolysis for o-nitrobenzyloxycarbonyl.

Protecting groups may also include different oxidation states of a chemical group. An example of such a protecting group is a nitro group, which may readily be reduced to an amino group. The amino group may be reactive under the reaction conditions of a synthetic step whereas the corresponding nitro group may be inert to the reaction conditions. In such cases, the synthetic step may be performed with a nitro group in the place of the amino group. The nitro group may be reduced to the desired amino group at a later point in the synthesis.

Further examples of protecting groups can be found in Green and Wuts, *Protecting Groups in Organic Synthesis,* 3rd edition, published by John Wiley and Sons, New York (1999) and Harrison et al., "Compendium of Synthetic Organic Methods," Vols. 1-8 by John Wiley and Sons (1971-1996), the entire disclosures of which are incorporated herein by reference.

One example of the application of protecting groups is shown in Scheme 5, for the preparation of the compound (E)-5-((2,4,6-trimethoxystyrylsulfonyl)methyl)-2-methoxybenzenamine 14:

Scheme 5

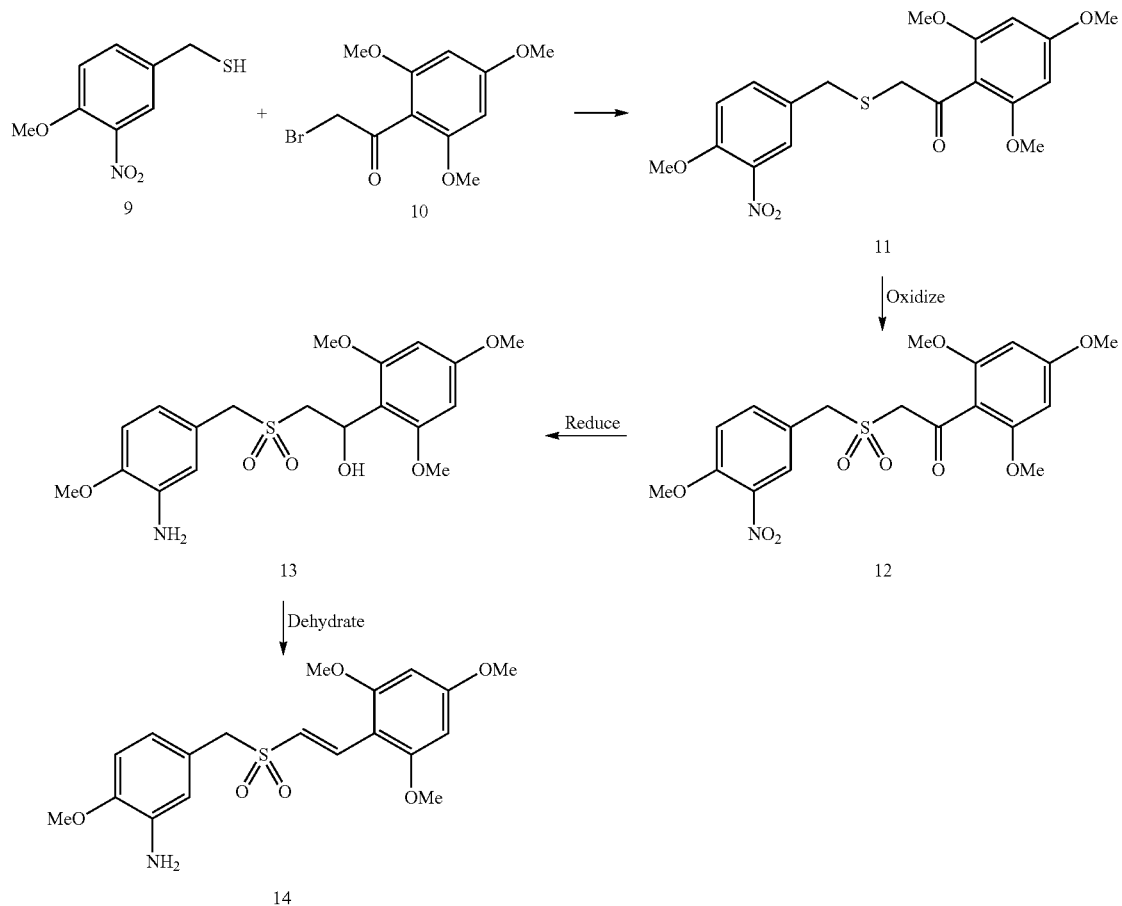

According to Scheme 5, (4-methoxy-3-nitrophenyl)methanethiol 10 (an aromatic mercaptan according to Formula IIb) is reacted with 2-bromo-1-(2,4,6-trimethoxyphenyl)ethanone (a compound according to Formula IIa) to form 2-(4-methoxy-3-nitrobenzylthio)-1-(2,4,6-trimethoxyphenyl) ethanone 11 (a sulfide according to Formula II). Suitable reaction conditions for this reaction are as described above for the reaction of a Formula IIa compound and a Formula IIb compound.

Compound 11 is reacted with an oxidizing agent capable of oxidizing a sulfide to a sulfone, thereby forming 2-(4-methoxy-3-nitrobenzylsulfonyl)-1-(2,4,6-trimethoxyphenyl) ethanone 12 (a sulfone compound according to Formula II). Suitable oxidation conditions are as described above for the oxidation of a Formula II sulfide compound to a Formula II sulfone compound.

Compound 12 is reacted under conditions sufficient to reduce the ketone moiety to a secondary alcohol thereby forming 2-(3-amino-4-methoxybenzylsulfonyl)-1-(2,4,6-trimethoxyphenyl)ethanol, 13 (a compound according to Formula III). The reduction is performed under any conditions sufficient to reduce the ketone moiety of compound 12 to a secondary alcohol, and sufficient to reduce the nitro moiety of compound 12 to an amine. The reduction may be performed, for example, by hydrogenation in the presence of a hydrogenation catalyst. The hydrogenation is preferably carried out in the presence of a solvent. Suitable solvents include, for example, ethanol, methanol, THF, and acetic acid. Suitable hydrogenation catalysts include platinum, palladium, nickel and ruthenium catalysts. The hydrogenation reaction is preferably performed at a temperature in the range from about 0° C. to about 100° C., more preferably from about 10° C. to about 60° C., most preferably from about 20° C. to about 30° C. The hydrogenation reaction is preferably performed at a hydrogen pressure in the range from about 1 to about 100 atmospheres, more preferably from about 1 to about 10 atmospheres, most preferably from about 1 to about 3 atmospheres.

Alternatively, reduction of the ketone moiety and the nitro moiety of compound 12 may be performed as separate reaction steps. For example, the ketone moiety may be reduced by reaction with a hydride reagent such as sodium borohydride, lithium aluminum hydride and sodium bis(2-methoxyethoxy)aluminum hydride as described herein. Following the reduction of the ketone moiety, the nitro moiety may be reduced, for example by catalytic hydrogenation as described above, or by other procedure such as, for example reaction with zinc and acetic acid, or tin and aqueous HCl, or by other methods of aromatic nitro group reduction known in the art.

Compound 13 is reacted under conditions sufficient to dehydrate the secondary alcohol moiety of compound 13 to form (E)-5-(2,4,6-trimethoxystyrylsulfonyl)methyl)-2-methoxybenzenamine, 14 (a compound according to Formula I). Suitable conditions under which compound 13 may be dehydrated to form compound 14 are as described above for the dehydration of a Formula III compound to form a Formula I compound.

The practice of the invention is illustrated by the following non-limiting examples.

EXAMPLES

I. Examples 1-6

Compounds according to Formula I are prepared according to Scheme 6:

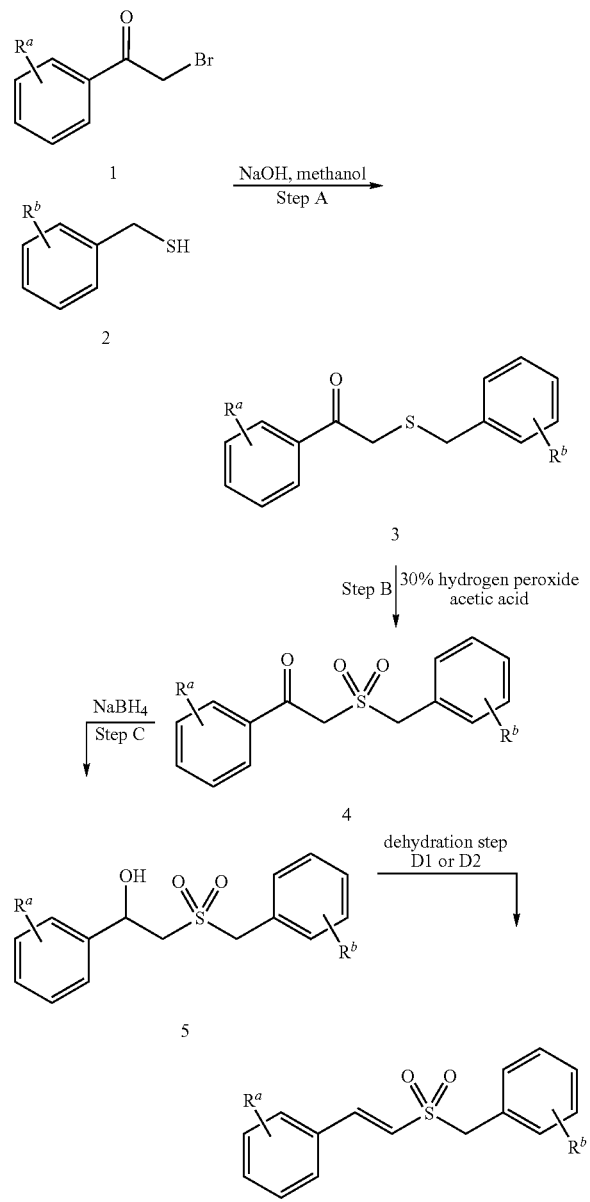

Step A. Preparation of Substituted Phenacyl Arylmethanesulfide 3:

A benzyl or substituted benzyl mercaptan 1 (10 mmol) is added slowly to a solution of sodium hydroxide (10 mmol) in methanol (50 mL) at ambient temperature (25° C.) to form a solution. To this solution is added, portion-wise, a phenacyl or substituted phenacyl bromide 2 (10 mmol). Following the addition, the resulting mixture is heated at reflux temperature with stirring for 8 hours. The reaction is monitored by TLC to determine when the reaction is complete. When the reaction is complete, the solution is then cooled to ambient temperature (25° C.) and poured onto crushed ice (about 200 g). The crude product phenacyl arylmethanesulfide 3 precipitates and is collected by filtration and dried under vacuum. The phenacyl arylmethanesulfide is used for the next step without additional purification.

Step B. Preparation of Substituted Phenacyl Arylmethanesulfone 4:

To a solution of phenacyl arylmethanesulfide 3 (5 g) in glacial acetic acid (40 mL), is added 30% hydrogen peroxide (10 mL). The resulting solution is stirred at ambient temperature (25° C.) for 8 hours. The reaction is monitored by TLC to determine when the reaction is complete. When the reaction is complete, the solution is then poured onto crushed ice (about 200 g). A solid precipitates and is separated by filtration. The separated solid is recrystallized from 2-propanol to yield the purified product phenacyl arylmethanesulfone 4. The intermediate phenacyl arylmethanesulfone 4 is a compound according to Formula II.

Step C. Preparation of 1-Aryl-2-arylmethanesulfonyl-ethanol 5:

To a solution of phenacyl arylmethanesulfone 4 (10 mmol) in tetrahydrofuran (30 mL) is added sodium borohydride (20 mmol). The resulting mixture is stirred for 8 h at ambient temperature (25° C.). The reaction is monitored by TLC to determine when the reaction is complete. After completion of the reaction, the solvent is removed under vacuum to form a residue. Water (200 mL) is added to the residue. A solid precipitate forms. The precipitate is separated by filtration, washed with water (3×25 mL) and purified by column chromatography to yield the purified product 1-aryl-2-arylmethanesulfonyl-ethanol 5. Intermediate 1-aryl-2-arylmethanesulfonyl-ethanol 5 is a compound of the invention according to Formula III.

Step D1. Preparation of (E)-styryl benzylsulfone 6 (Method 1):

Boron trifluoride etherate (5 mmol) is added to an acetic anhydride (10 mL) solution of the 1-aryl-2-arylmethanesulfonyl-ethanol 5 (5 mmol) at 0° C. The resulting mixture is stirred for 0.5 h. The mixture is then poured into chloroform (25 mL). The organic layer is separated. The organic layer is washed with saturated aqueous NaHCO$_3$ (2×25 mL), and water (2×25 mL). The organic layer is then dried over sodium sulfate, filtered and concentrated under vacuum to yield a residue. The residue is recrystallized from 2-propanol to yield the desired (E)-styryl benzylsulfone product 6.

Step D2. Preparation of (E)-styryl benzylsulfone 6 (Method 2):

To a cooled solution of the phenacyl arylmethanesulfone 4 (5 mmol) in ethanol (50 mL), is added sodium borohydride (5 mmol). The resulting mixture is stirred for 1 h at ambient temperature (25° C.). A few crystals of bromocresol blue are added as a pH indicator and the resulting mixture is heated to reflux temperature and maintained at reflux temperature for 1 h. Concentrated HCl is added dropwise to the heated solution until the color of the solution changes to yellow. After refluxing for 5 h, the solution is diluted with water (50 mL). The diluted mixture is cooled to 0° C. and stirred for 0.5 h. A solid precipitate forms. The precipitate is separated by filtration, washed with water (2×25 mL), and dried to yield the desired (E)-styryl benzylsulfone product 6. (E)-styryl benzylsulfone product 6 is a compound according to Formula I prepared according to the process of the invention.

The compounds of Examples 1-6 were prepared according to the procedures of Steps A, B, C, D1 and D2. Table 1 lists the intermediate phenacyl arylmethanesulfones 4 which were prepared according to Step B as intermediates in the preparation of the compounds of Examples 1-6.

TABLE 1

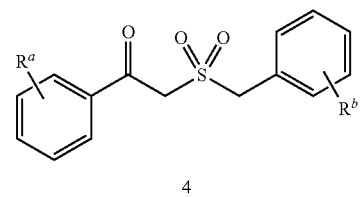

4

Intermediates 4 in the Preparation of Example 1-6 Compounds

| Example # | $R^a$ | $R^b$ | Melting point (° C.) | Yield (%) |
|---|---|---|---|---|
| 1 | 4-Cl | 4-OCH₃ | 154-156 | 77 |
| 2 | H | 4-OCH₃ | 112-114 | 82 |
| 3 | 4-OCH₃ | 4-OCH₃ | 132-134 | 69 |
| 4 | 4-F | 4-Cl | Not done | 74 |
| 5 | 4-Cl | 4-Cl | 156-158 | 82 |
| 6 | 4-Br | 4-Cl | 172-174 | 86 |

Table 2 lists the intermediate 1-aryl-2-arylmethanesulfonyl-ethanols 5 prepared according to Step C as intermediates in the preparation of the compounds of Examples 1-6.

TABLE 2

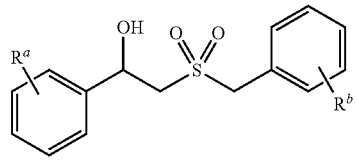

5

Intermediates 5 in the Preparation of Example 1-6 Compounds

| Example # | $R^a$ | $R^b$ | Melting point (° C.) | Yield (%) |
|---|---|---|---|---|
| 1 | 4-Cl | 4-OCH₃ | 164-166 | 71 |
| 2 | H | 4-OCH₃ | 186-188 | 68 |
| 3 | 4-OCH₃ | 4-OCH₃ | 170-174 | 62 |
| 4 | 4-F | 4-Cl | 144-146 | 74 |
| 5 | 4-Cl | 4-Cl | 168-169 | 78 |
| 6 | 4-Br | 4-Cl | 160-162 | 70 |

Table 3 lists the (E)-styryl benzylsulfone products 6 which were prepared according to Step D1.

TABLE 3

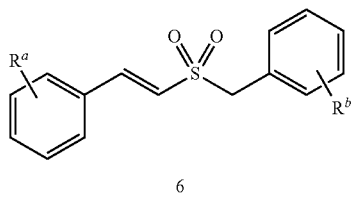

6

Example 1-6 Compounds (6)

| Ex. # | Compound Name | $R^a$ | $R^b$ | Melting point (° C.) | Yield (%) |
|---|---|---|---|---|---|
| 1 | 1-((E)-2-(4-methoxybenzyl-sulfonyl)vinyl)-4-chlorobenzene | 4-Cl | 4-OCH₃ | 176-177 | 64 |
| 2 | 1-((E)-2-(4-methoxybenzyl-sulfonyl)vinyl)benzene | H | 4-OCH₃ | Not done | Not done |
| 3 | (E)-1-((4-methoxystyryl-sulfonyl)-methyl)-4-methoxybenzene | 4-OCH₃ | 4-OCH₃ | 150-152 | 58 |
| 4 | (E)-1-((4-fluorostyryl-sulfonyl)-methyl)-4-chlorobenzene | 4-F | 4-Cl | 161-162 | 69 |
| 5 | (E)-1-((4-chlorostyryl-sulfonyl)-methyl)-4-chlorobenzene | 4-Cl | 4-Cl | 170-171 | 61 |
| 6 | (E)-1-((4-bromostyryl-sulfonyl)-methyl)-4-chlorobenzene | 4-Br | 4-Cl | 158-160 | 72 |

II. Examples 7-10

Compounds according to Formula I are alternatively prepared according to Scheme 7, wherein Steps C and D1/D2 are performed according to the same procedures described for Examples 1-6:

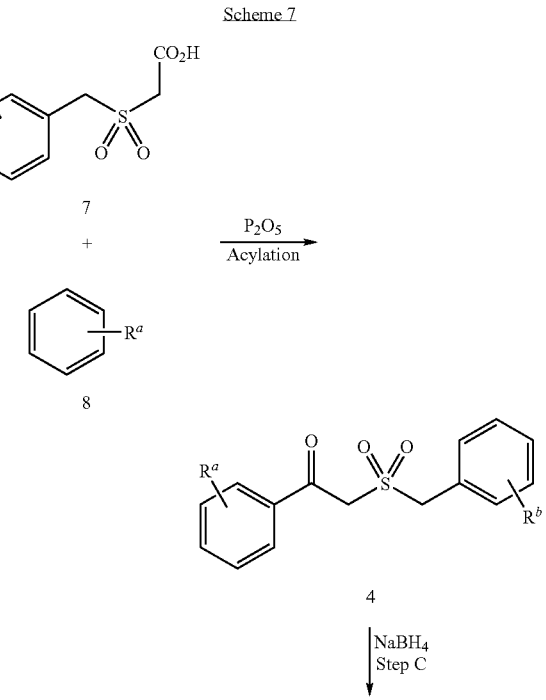

Scheme 7

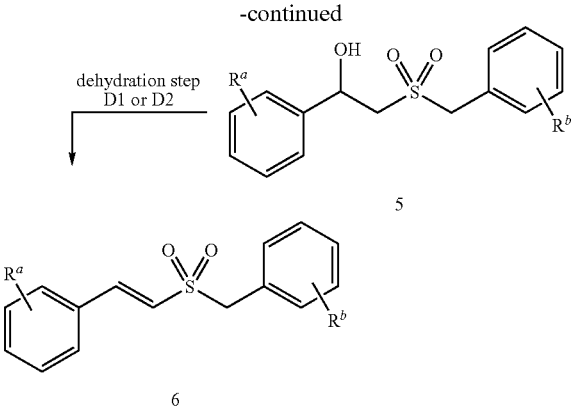

Step A2. Preparation of Phenacyl Arylmethanesulfone 4

Benzyl sulfonyl acetic acid 7 (4.1 mmol) is added to a phenyl compound 8 (30 mL). To this mixture is added phosphorous pentoxide (4.0 g). The resulting reaction mixture is heated to 81° C. and maintained at that temperature until the reaction is complete. The reaction is monitored by TLC. When the reaction is complete by TLC analysis, the reaction mixture is cooled to ambient temperature (25° C.). Dichloromethane (25 mL) is added to the cooled reaction mixture. A viscous solid precipitate forms. The precipitate is separated by filtration. The precipitate is washed with dichloromethane (2×50 mL). The filtrate and the dichloromethane washes are combined and concentrated under vacuum to yield a residue. The residue is purified by column chromatography to yield the purified phenacyl arylmethanesulfone compound 4 according to Formula II.

Table 4 lists the intermediate phenacyl arylmethanesulfones 4 which were prepared according to Step A2 as chemical intermediates.

TABLE 4

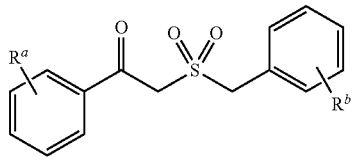

4

Intermediates 4 in the Preparation of Example 7-10 Compounds

| Example # | $R^a$ | $R^b$ | Melting point (° C.) | Yield (%) |
|---|---|---|---|---|
| 7 | H | 4-F | 141-142 | 88 |
| 8 | H | 4-Cl | 150-154 | 92 |
| 9 | H | 4-I | 159-160 | 83 |
| 10 | 4-F | 4-F | 148-150 | 65 |

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A process for preparing a compound according to Formula I, or a salt thereof:

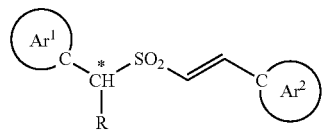

wherein:
Ar$^1$ and Ar$^2$ are independently selected from substituted and unsubstituted aryl and substituted and unsubstituted heteroaryl;
R is —H or —(C$_1$-C$_8$)hydrocarbyl; and
* indicates that, when R is other than —H, the configuration of the substituents on the carbon atom is (R)—, (S)— or any mixture of (R)— and (S)—;

said process comprising the steps of:
(a) reacting a compound according to Formula II, or a salt thereof:

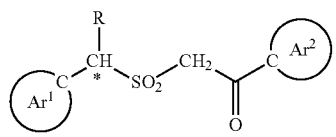

wherein, Ar$^1$, Ar$^2$, R and * are as defined above, under conditions sufficient to reduce the ketone moiety of the Formula II compound to a secondary alcohol, to form a compound according to Formula III, or a salt thereof:

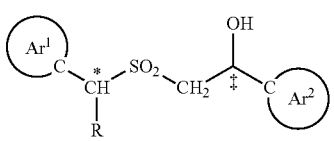

wherein Ar$^1$, Ar$^2$, * and R are as defined for compounds according to Formula I, and ‡ indicates that the configuration of the substituents on the designated carbon atom is (R)—, (S)— or any mixture of (R)— and (S)—;
(b) reacting said compound according to Formula III prepared in step (a), or a salt thereof, under conditions sufficient to dehydrate the secondary alcohol moiety of the Formula III compound to form a compound according to Formula I, or a salt thereof; and
(c) isolating said compound according to Formula I formed in step (b), or a salt thereof, from the reaction mixture of step (b).

2. A process according to claim 1, wherein:
substituents on substituted aryl and substituted heteroaryl Ar$^1$ are independently selected from the group consisting of halogen, —(C$_1$-C$_8$)hydrocarbyl, —C(=O)R$^2$, —NR$^2$$_2$, —NHC(=O)R$^3$, —NHSO$_2$R$^3$, —NH(C$_2$-C$_6$)alkylene-C(=O)R$^6$, —NHCR$^2$R$^4$C(=O)R$^6$, —C(=O)OR$^2$, —C(=O)NR$^2$$_2$, —NO$_2$, —OR$^2$, —OC(=O)R$^3$, —OSO$_2$R$^3$, —O(C$_2$-C$_6$)alkylene-C(=O)R$^6$, —OCR²R⁴C(=O)R⁶, —P(=O)(OR²)₂, —OP(=O)(OR²)₂, —O(C₂-C₆)alkylene-N((C₁-C₃)alkyl)₂, —NHC(=NH)NHR², —(C₁-C₆)haloalkyl, —O(C₁-C₆)haloalkyl and —N=CH—R⁷; and substituents on substituted aryl and substituted heteroaryl Ar² are independently selected from the group consisting of —(C₁-C₈)hydrocarbyl, —C(=O)R², halogen, —NO₂, —OR², —C(=O)OR², —NR²₂, —(C₁-C₆)haloalkyl and —O(C₁-C₆)haloalkyl;

wherein:

each R² is independently selected from the group consisting of —H and —(C₁-C₈)hydrocarbyl;

each R³ is independently selected from the group consisting of —(C₁-C₈)hydrocarbyl, —(C₁-C₈)hydrocarbyl, substituted and unsubstituted aryl, substituted and unsubstituted heterocyclyl(C₁-C₃)alkyl, substituted and unsubstituted heteroaryl(C₁-C₃)alkyl, —(C₂-C₁₀)heteroalkyl, —(C₁-C₆)haloalkyl, —CR²R⁴NHR⁵, —NR²₂, —(C₁-C₃)alkyleneNH₂, —(C₁-C₃)alkylene-N((C₁-C₃)alkyl)₂, —(C₁-C₃)perfluoroalkylene-N((C₁-C₃)alkyl)₂, —(C₁-C₃)alkylene-N⁺((C₁-C₃)alkyl)₃, —(C₁-C₃)alkylene-N⁺(CH₂CH₂OH)₃, —(C₁-C₃)alkylene-OR², —(C₁-C₄)alkylene-CO₂R², —(C₁-C₄)alkylene-C(=O)halogen, halo(C₁-C₃)alkyl-, —(C₁-C₃)alkylene-C(=O)(C₁-C₃)alkyl, and —(C₁-C₄)perfluoroalkylene-CO₂R²;

each R⁴ is independently selected from the group consisting of —H, —(CH₂)₃—NH—C(NH₂)(=NH), —CH₂C(=O)NH₂, —CH₂CO₂R², —CH₂SH, —(CH₂)₂C(=O)—NH₂, —(CH₂)₂CO₂R², —CH₂-(2-imidazolyl), —(CH₂)₄—NH₂, —(CH₂)₂—S—CH₃, phenyl, —CH₂-phenyl, —CH₂—OH, —CH(OH)—CH₃, —CH₂-(3-indolyl), and —CH₂-(4-hydroxyphenyl);

each R⁵ is independently selected from the group consisting of —H, —C(=O)(C₁-C₇)hydrocarbyl and a carboxy terminally-linked peptidyl residue containing from 1 to 3 amino acids in which the terminal amino group of the peptidyl residue is present as a functional group selected from the group consisting of —NH₂, —NHC(=O)(C₁-C₆)alkyl, —NH(C₁-C₆)alkyl, —N((C₁-C₆)alkyl)₂ and —NHC(=O)O(C₁-C₇)hydrocarbyl;

each R⁶ is independently selected from the group consisting of —OR², —NR²₂, and an amino terminally-linked peptidyl residue containing from 1 to 3 amino acids in which the terminal carboxyl group of the peptidyl residue is present as a functional group selected from the group consisting of —CO₂R² and —C(=O)NR²₂; and each R⁷ is independently selected from the group consisting of substituted and unsubstituted aryl and substituted and unsubstituted heteroaryl;

provided that the highest number of substituents on Ar¹ and Ar² is equal to the number of substitutable hydrogen atoms in the ring to which the substituents are attached.

3. A process according to claim 1, wherein the compound according to Formula II comprises at least one nitro group as a substituent on at least one of Ar¹ and Ar².

4. A process according to claim 3 further comprising the step of reducing the nitro group to an amine.

5. A process according to claim 3, wherein the reaction conditions in step (a) which are sufficient to reduce the ketone moiety of the Formula II compound to a secondary alcohol are also sufficient to reduce the nitro group to an amine.

6. A process according to claim 1, wherein the compound according to Formula II, or a salt thereof, is prepared by a process comprising the steps of:

(a) reacting a compound according to Formula IIc, or a salt thereof:

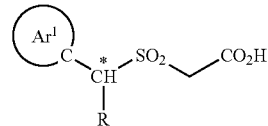

wherein Ar¹, R and * are as defined in claim 1, with a compound according to Formula IId, or a salt thereof:

wherein Ar² is as defined in claim 1, under conditions suitable for electrophilic acylation of the aromatic ring of Ar²; and (b) isolating a compound according to Formula II, or a salt thereof, from the reaction products of step (a).

7. A process according to claim 1 wherein the compound of Formula II, or a salt thereof, is prepared by the steps of:

(a) reacting a compound according to Formula IIa, or a salt thereof:

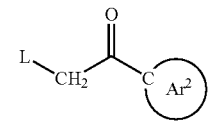

wherein Ar² is selected from substituted and unsubstituted aryl and substituted and unsubstituted heteroaryl, and L is a leaving group, with a compound according to Formula IIb, or a salt thereof:

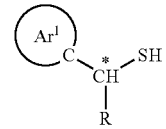

wherein Ar¹ is selected from substituted and unsubstituted aryl and substituted and unsubstituted heteroaryl;

R is —H or —(C₁-C₈)hydrocarbyl; and

* indicates that, when R is other than —H, the configuration of the substituents on the carbon atom is (R)—, (S)— or any mixture of (R)— and (S)—, to form a compound according to Formula II, or a salt thereof; and (b) reacting the compound according to Formula II formed in step (a), or a salt thereof, with an oxidizing agent capable of oxidizing a sulfide to a sulfone to form a compound according to Formula II, or a salt thereof.

8. A process according to claim 1, wherein the prepared compound according to Formula I is selected from the group consisting of (E)-5-(2,4,6-trimethoxystyrylsulfonyl)methyl)-2-methoxyphenol; (E)-2-(5-((2,4,6-trimethoxystyrylsulfonyl)methyl)-2-methoxyphenylamino)propanoic acid; (E)-5-((2,4,6-trimethoxystyrylsulfonyl)methyl)-2-methoxybenzenamine; (E)-2-(5-((2,4,6-trimethoxystyrylsulfonyl)methyl)-2-methoxyphenylamino)

acetic acid; 1-((E)-2-(benzylsulfonyl)vinyl)-4-fluorobenzene; 1-((E)-2-(benzylsulfonyl)vinyl)-4-iodobenzene; 1-((E)-2-(benzylsulfonyl)vinyl)-4-chlorobenzene; (E)-1-((4-chlorostyrylsulfonyl)methyl)-4-methoxybenzene; (E)-1-methoxy-4-((styrylsulfonyl)methyl)benzene; (E)-1-((4-methoxystyrylsulfonyl)methyl)-4-methoxybenzene; (E)-1-((4-chlorostyrylsulfonyl)-methyl)-4-chlorobenzene; (E)-1-((4-fluorostyrylsulfonyl)methyl)-4-chlorobenzene; (E)-1-((4-bromostyrylsulfonyl)methyl)-4-chlorobenzene; (E)-2-(5-((2,4,6-trimethoxystyryl-sulfonyl)methyl)-2-methoxyphenylamino)-2-phenylacetic acid; and salts thereof.

9. A process according to claim 5 for preparing the Formula I compound, (E)-5-((2,4,6-trimethoxystyrylsulfonyl)methyl)-2-methoxybenzenamine, or a salt thereof, said process comprising the steps of:

(a) reacting the Formula II compound 2-(4-methoxy-3-nitrobenzylsulfonyl)-1-(2,4,6-trimethoxyphenyl)ethanone under conditions sufficient to reduce the ketone moiety of said Formula II compound to a secondary alcohol, and sufficient to reduce the nitro moiety of said Formula II compound to an amine, to form the Formula III compound, 2-(3-amino-4-methoxybenzylsulfonyl)-1-(2,4,6-trimethoxyphenyl)ethanol, or a salt thereof; and (b) reacting the 2-(3-amino-4-methoxybenzylsulfonyl)-1-(2,4,6-trimethoxyphenyl)ethanol formed in step (a) under conditions sufficient to dehydrate the secondary alcohol moiety of said Formula III compound to form the Formula I compound, (E)-5-((2,4,6-trimethoxystyrylsulfonyl)methyl)-2-methoxybenzenamine, or a salt thereof;

wherein:
said 2-(4-methoxy-3-nitrobenzylsulfonyl)-1-(2,4,6-trimethoxyphenyl)ethanone is prepared by a process comprising the steps of:

(c) reacting 4-methoxy-3-nitrophenyl)methanethiol, or a salt thereof, with 2-bromo-1-(2,4,6-trimethoxyphenyl)ethanone or 2-chloro-1-(2,4,6-trimethoxyphenyl)ethanone, to form 2-(4-methoxy-3-nitrobenzylthio)-1-(2,4,6-trimethoxyphenyl)ethanone; and (d) reacting the 2-(4-methoxy-3-nitrobenzylthio)-1-(2,4,6-trimethoxy-phenyl)ethanone formed in step (c) with an oxidizing agent capable of oxidizing a sulfide to a sulfone, to form said 2-(4-methoxy-3-nitrobenzylsulfonyl)-1-(2,4,6-trimethoxyphenyl)ethanone.

\* \* \* \* \*